United States Patent
Sauer et al.

(10) Patent No.: US 11,344,293 B2
(45) Date of Patent: *May 31, 2022

(54) LOADER FOR SURGICAL SUTURING

(71) Applicant: LSI Solutions, Inc., Victor, NY (US)

(72) Inventors: Jude S. Sauer, Pittsford, NY (US); Angelo John Martellaro, Victor, NY (US)

(73) Assignee: LSI Solutions, Inc., Victor, NY (US)

( * ) Notice: Subject to any disclaimer, the term of this patent is extended or adjusted under 35 U.S.C. 154(b) by 276 days.

This patent is subject to a terminal disclaimer.

(21) Appl. No.: 16/556,503

(22) Filed: Aug. 30, 2019

(65) Prior Publication Data

US 2020/0078005 A1     Mar. 12, 2020

Related U.S. Application Data

(63) Continuation of application No. 15/625,451, filed on Jun. 16, 2017, now Pat. No. 10,433,834.

(60) Provisional application No. 62/350,750, filed on Jun. 16, 2016.

(51) Int. Cl.
| | |
|---|---|
| *A61B 17/04* | (2006.01) |
| *A61B 17/06* | (2006.01) |
| *A61B 17/062* | (2006.01) |
| *A61B 17/00* | (2006.01) |

(52) U.S. Cl.
CPC ...... *A61B 17/0469* (2013.01); *A61B 17/0482* (2013.01); *A61B 17/0483* (2013.01); *A61B 17/0625* (2013.01); *A61B 17/06066* (2013.01); *A61B 2017/0053* (2013.01); *A61B 2017/0608* (2013.01)

(58) Field of Classification Search
CPC ............ A61B 17/0469; A61B 17/0482; A61B 17/0483; A61B 17/06066; A61B 17/06004; A61B 2017/0053; A61B 2017/047; A61B 2017/0479; A61B 2017/0608

See application file for complete search history.

(56) References Cited

U.S. PATENT DOCUMENTS

| | | |
|---|---|---|
| 6,533,796 B1 | 3/2003 | Sauer |
| 2011/0046642 A1 | 2/2011 | McClurg et al. |
| 2014/0141208 A1 | 9/2014 | Oldham et al. |

(Continued)

FOREIGN PATENT DOCUMENTS

WO       0230294       4/2002

OTHER PUBLICATIONS

Web Page: Endoevolution, LLC. Endo360 Technology; http://www.endoevolution.com/endo360/technology/ :Printed on Aug. 23, 2017, Apparent Copyright Jan. 1, 2017.

(Continued)

*Primary Examiner* — Diane D Yabut
(74) *Attorney, Agent, or Firm* — Michael E. Coyne

(57) ABSTRACT

A loader for a surgical suturing instrument is disclosed. The loader has a head having a protrusion configured to be releasably held by a tissue bite area of a surgical suturing instrument. The loader also has a tube interface. The loader further has one or more ferrule holders. The loader also has one or more ferrules, each corresponding to and held by one of the one or more ferrule holders and coupled to a suture end that leads from a tube releasably held by the tube interface.

14 Claims, 26 Drawing Sheets

(56) References Cited

U.S. PATENT DOCUMENTS

2015/0282805 A1 10/2015 Sauer
2016/0000422 A1* 1/2016 Harrison ............ A61B 17/0625
  606/144

OTHER PUBLICATIONS

Sep. 18, 2018 Office Action; Yabut, Diane D.; for U.S. Appl. No. 15/625,451.
Mar. 29, 2019 Office Action; Yabut, Diane D.; for U.S. Appl. No. 15/625,451.

* cited by examiner

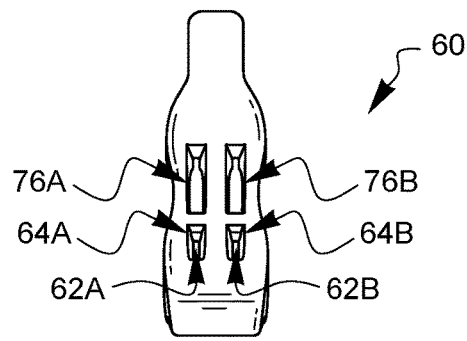
FIG. 5E
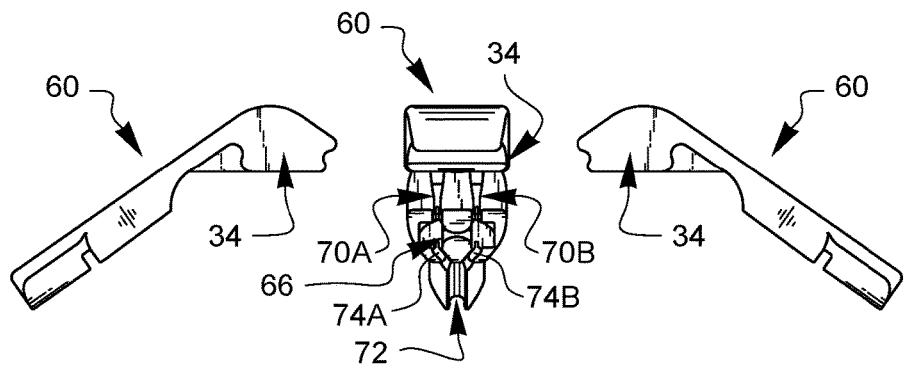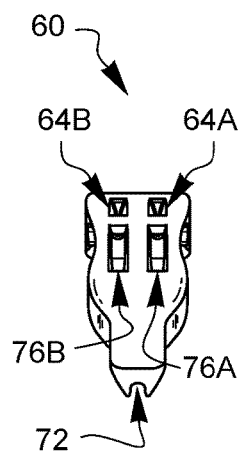
FIG. 5B  FIG. 5A  FIG. 5C  FIG. 5D
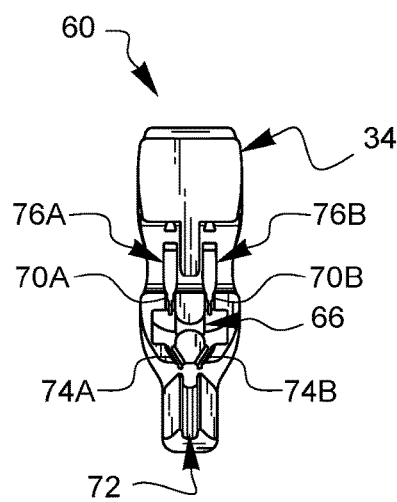
FIG. 5F

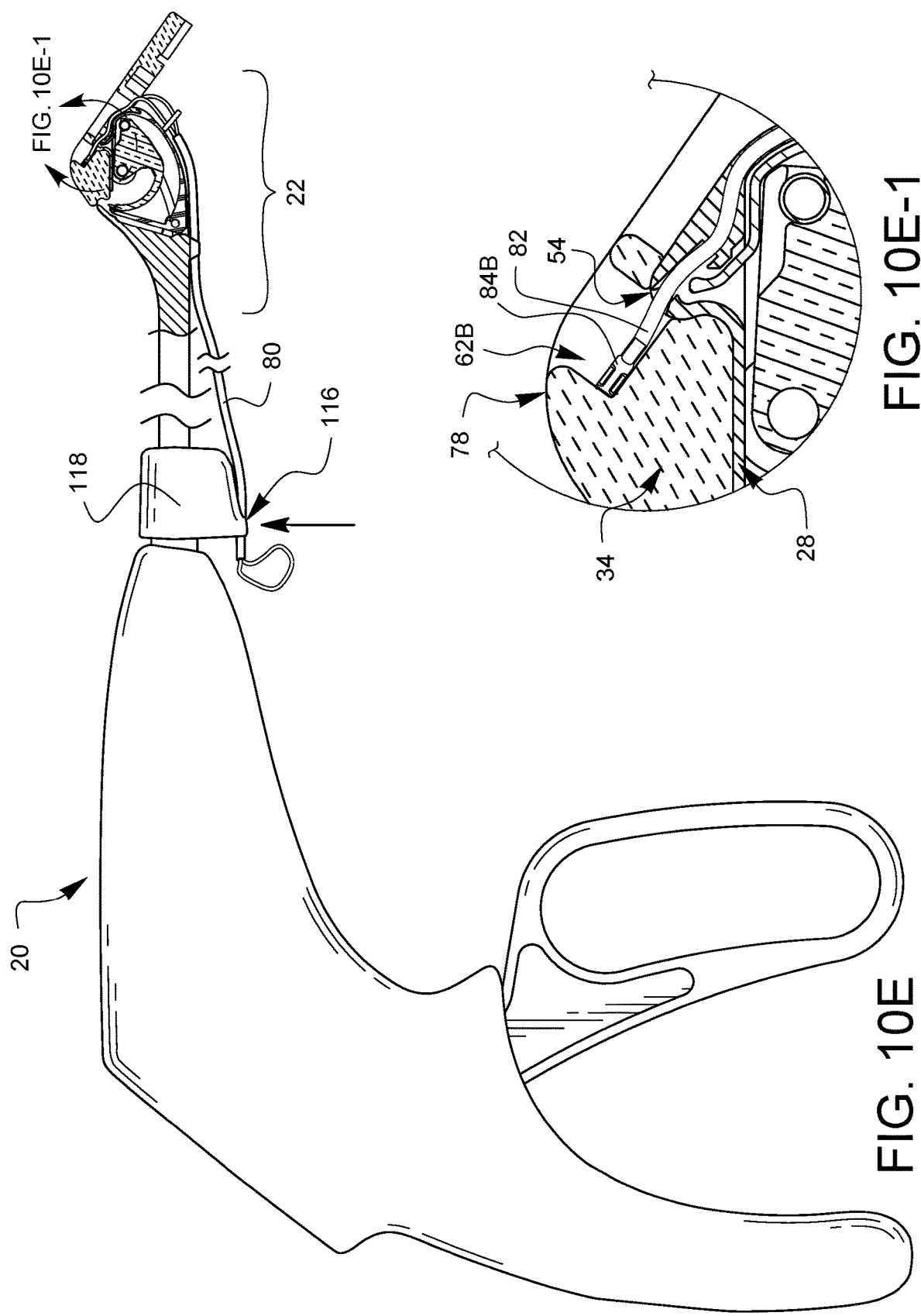

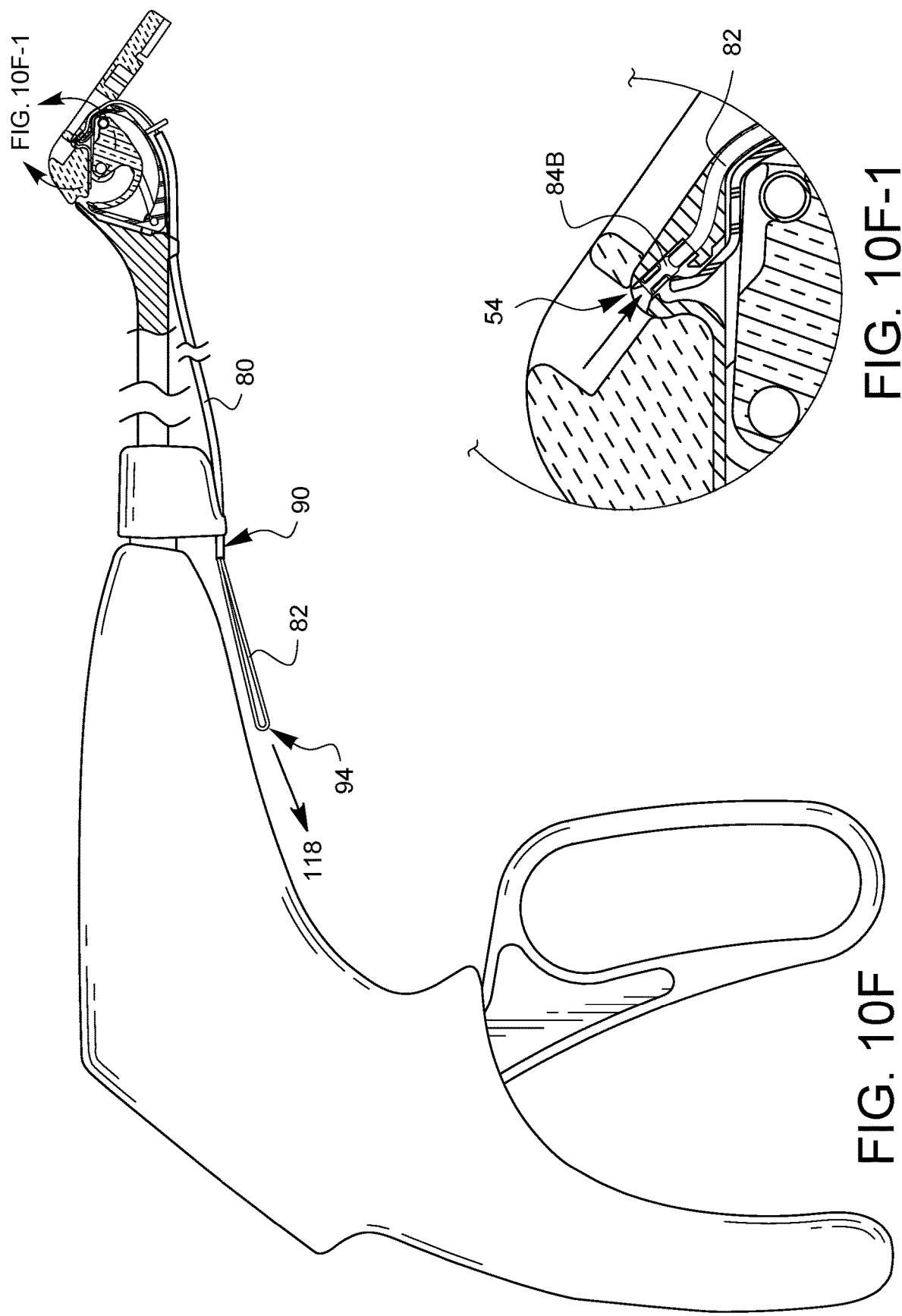

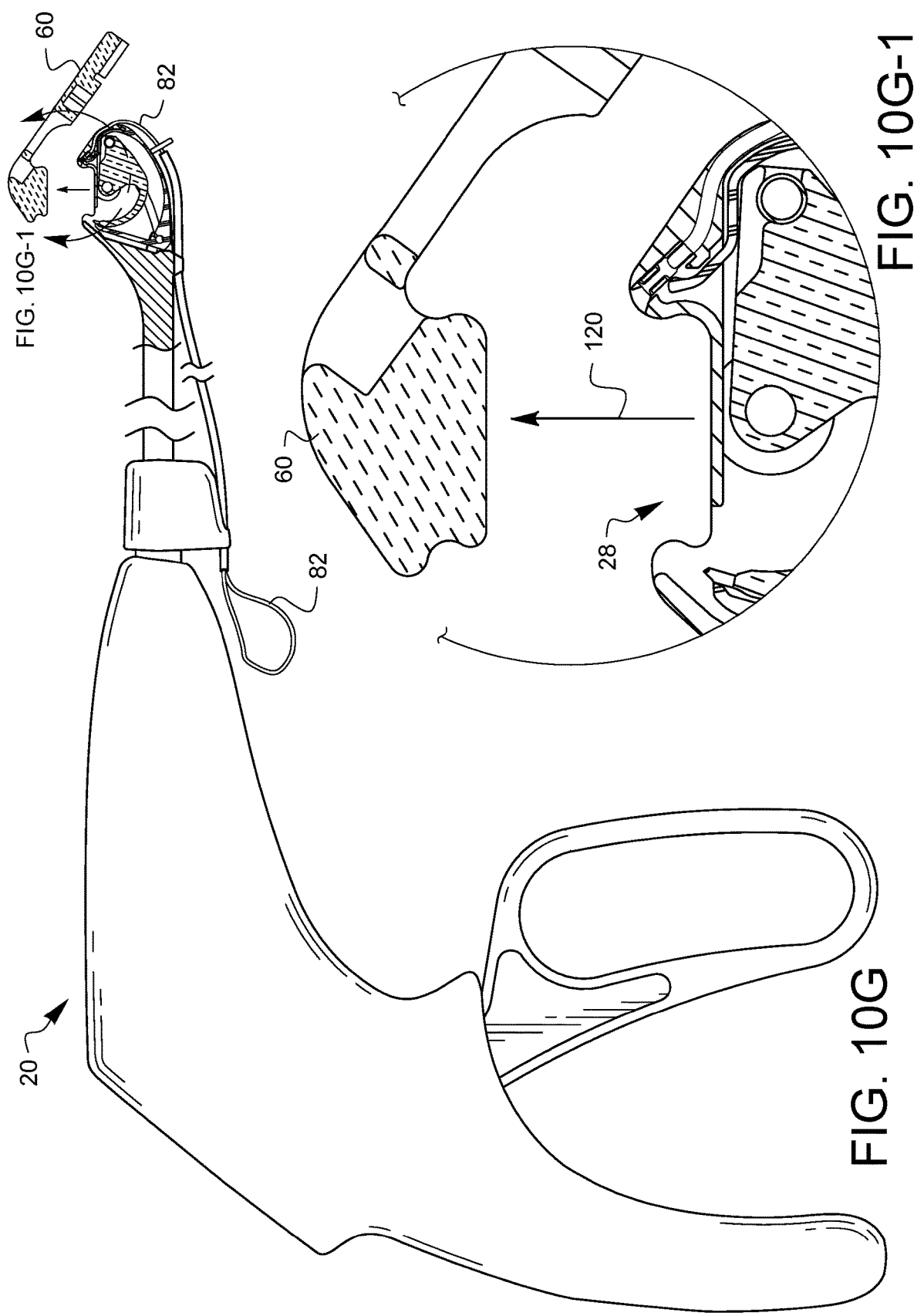

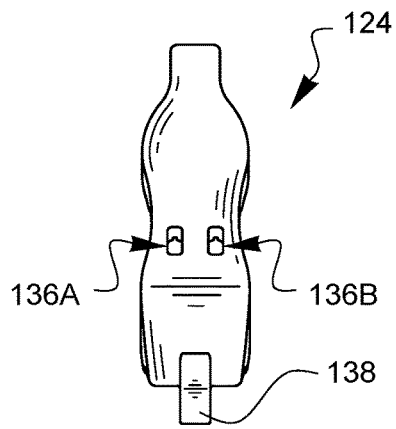
FIG. 13E
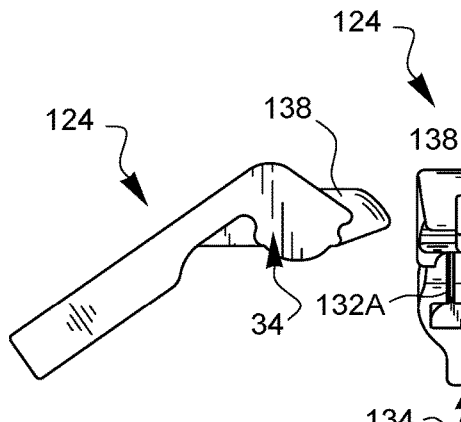
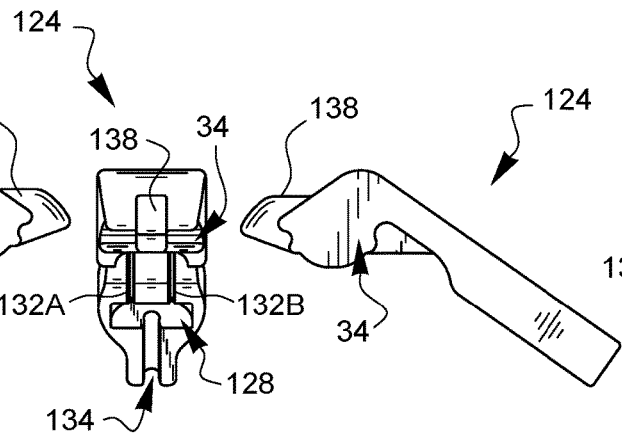
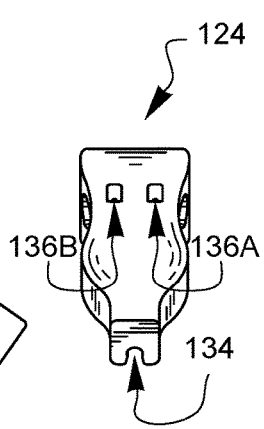
FIG. 13B  FIG. 13A  FIG. 13C  FIG. 13D
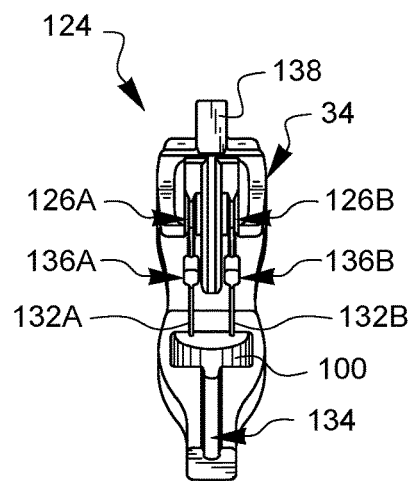
FIG. 13F

LOADER FOR SURGICAL SUTURING

RELATED APPLICATION

This application is a continuation of U.S. Non-Provisional patent application Ser. No. 15/625,451, filed Jun. 16, 2017, which claims priority to U.S. Provisional Patent Application No. 62/350,750, filed Jun. 16, 2016, each of which is incorporated by reference herein in its entirety.

FIELD

The claimed invention relates to surgical devices, and more specifically to loaders for surgical suturing devices and methods thereof.

BACKGROUND

Surgical suturing instruments have been developed that can place sutures remotely in laparoscopic or endoscopic procedures. The instruments vary in construction but generally include a suturing tip located at the distal end of an elongated rigid or flexible shaft. The suturing tip has one or more needles, usually two, that can be passed across a gap through a tissue section, in a process sometimes referred to as "taking a bite," engage a ferrule-tipped suture end and pull the end back through the tissue section so that the suture engages the tissue. The process is repeated at a second location (either in tissue or in a prosthetic material) and the suture is secured to bring the tissue sections or the tissue/prosthetic into apposition.

While surgical suturing instruments of the type just described are normally designed for disposal after use in a single procedure, they can be used multiple times during a procedure by reloading a new ferrule-tipped suture into the instrument and repeating the securing process.

Most commonly, the ferrule-tipped suture ends are disposed in cavities or recesses in the end of instrument which can be difficult to see, especially given the small size of the ferrules. Newer surgical suturing instruments may even have curved needle paths which can make it more difficult to see how a ferrule should be oriented in a ferrule-receiving cavity. Therefore, it would be desirable to have an improved apparatus for loading surgical suture into surgical suturing instruments.

SUMMARY

The claimed invention relates to surgical devices, and more specifically to loaders for surgical suturing devices and methods thereof.

BRIEF DESCRIPTION OF THE DRAWINGS

FIGS. 5A, 5B, 5C, 5D, 5E, and 5F are front, left side, right side, rear, top, and bottom elevational views respectively of the quick-load head of FIGS. 4A, 4B.

FIGS. 10A to 10G-1 illustrate one embodiment of using a loader, in this case, the loader of FIGS. 6A-6B to load ferrules into a surgical suturing instrument, such as the instrument of FIG. 1.

FIGS. 13A, 13B, 13C, 13D, 13E, and 13F are front, left side, right side, rear, top, and bottom elevational views respectively of the quick-load head of FIGS. 12A, 12B.

Figure 1:
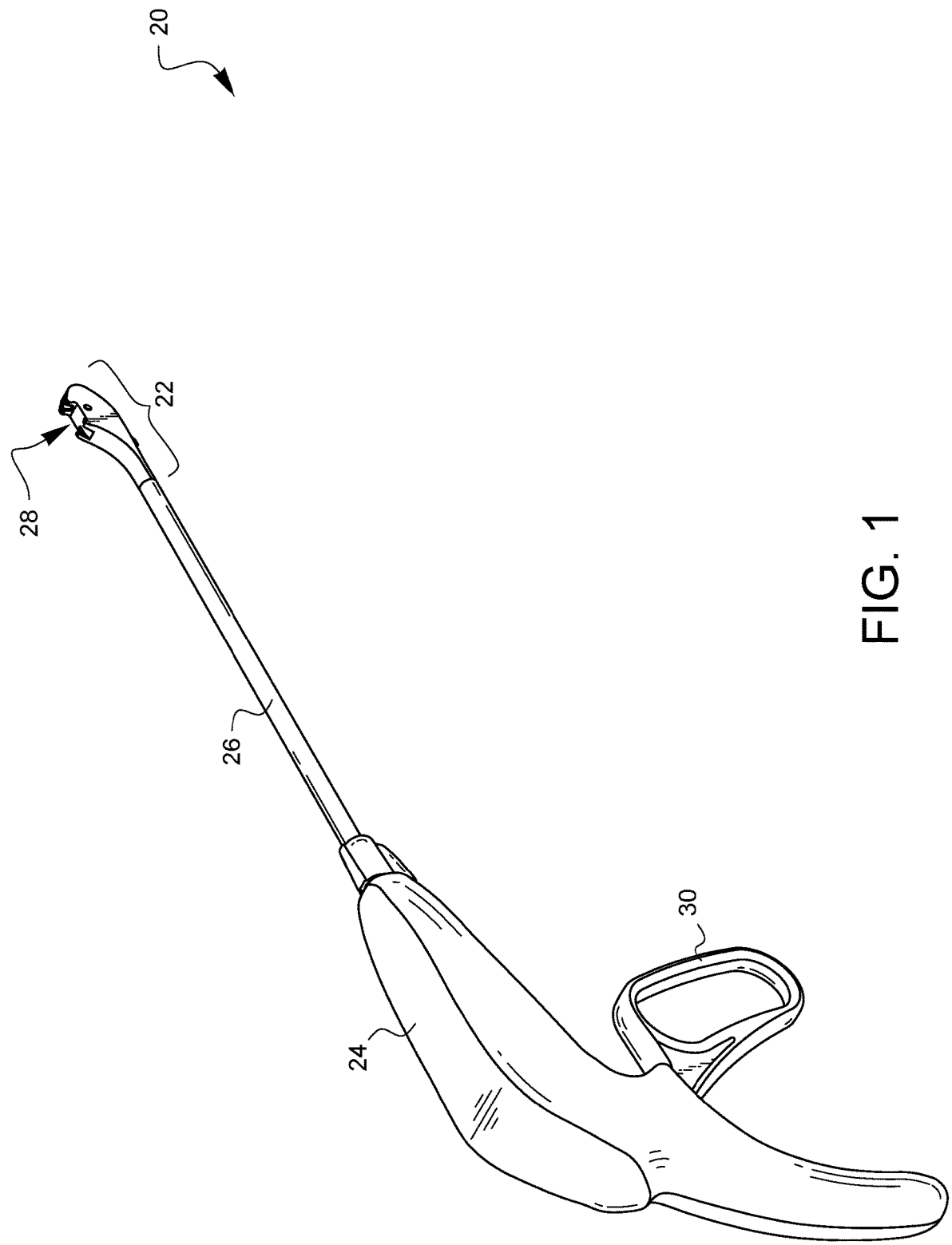
FIG. 1 is a perspective view of one embodiment of a surgical suturing instrument.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1 is a perspective view of one embodiment of a surgical suturing instrument 20. The suturing instrument 20 has a distal end 22 which is coupled to a housing 24 by a shaft 26. The distal end 22 has a tissue bite area 28 across which curved needles (not visible in this view) may traverse when a handle 30 is squeezed.

Figure 2:
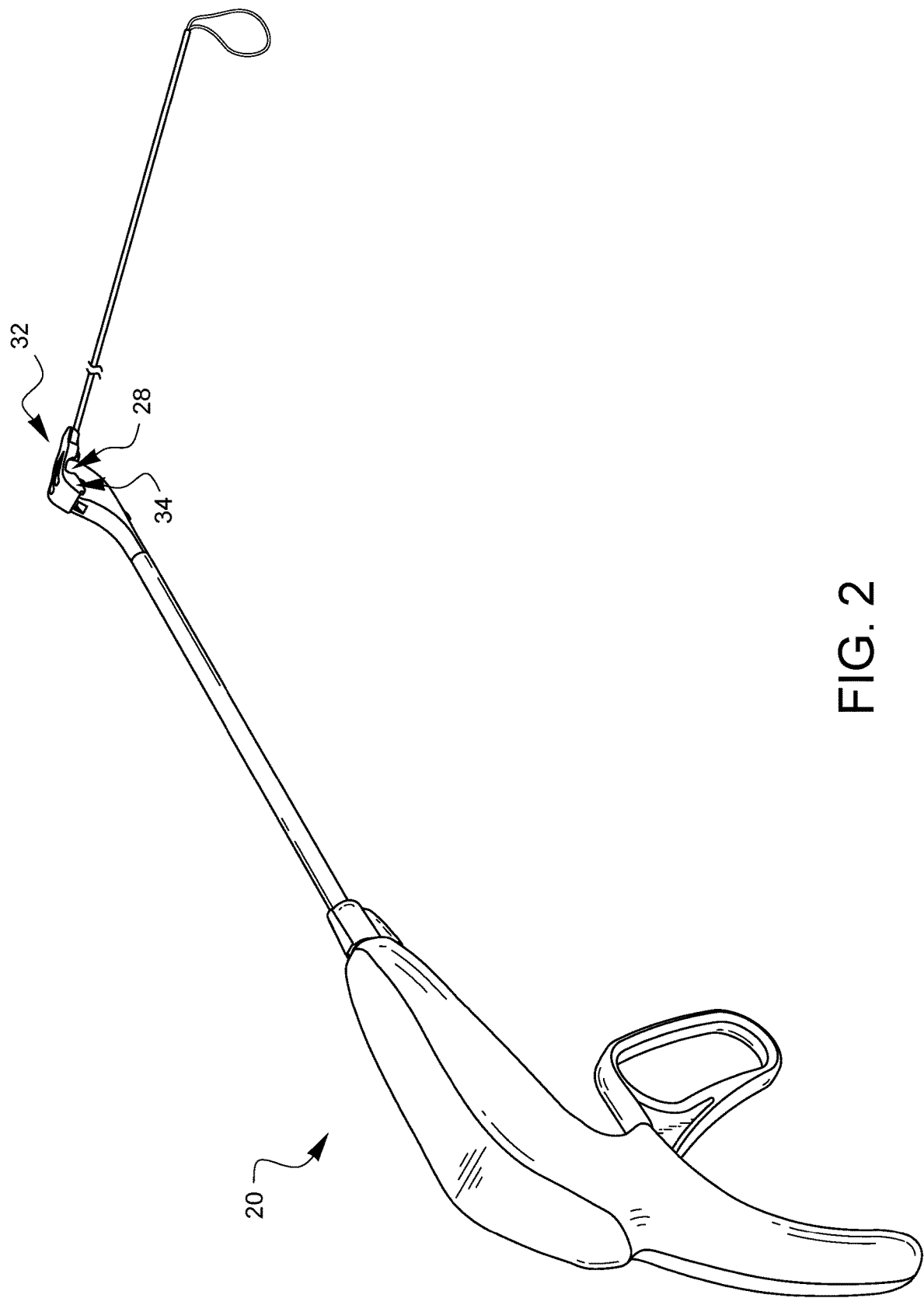
FIG. 2 is a perspective view of one embodiment of a loader for a surgical suturing instrument.

FIG. 2 is a perspective view of one embodiment of a loader 32 for a surgical suturing instrument 20. The loader 32 has a projection 34 for insertion into the tissue bite area 28 of the instrument 20. This configuration and mating will be discussed in more detail later in the specification, but first, the operation of the needles and ferrules within the surgical suturing instrument 20 will be discussed for more background with regard to FIGS. 3A-3C.

Figure 3A:
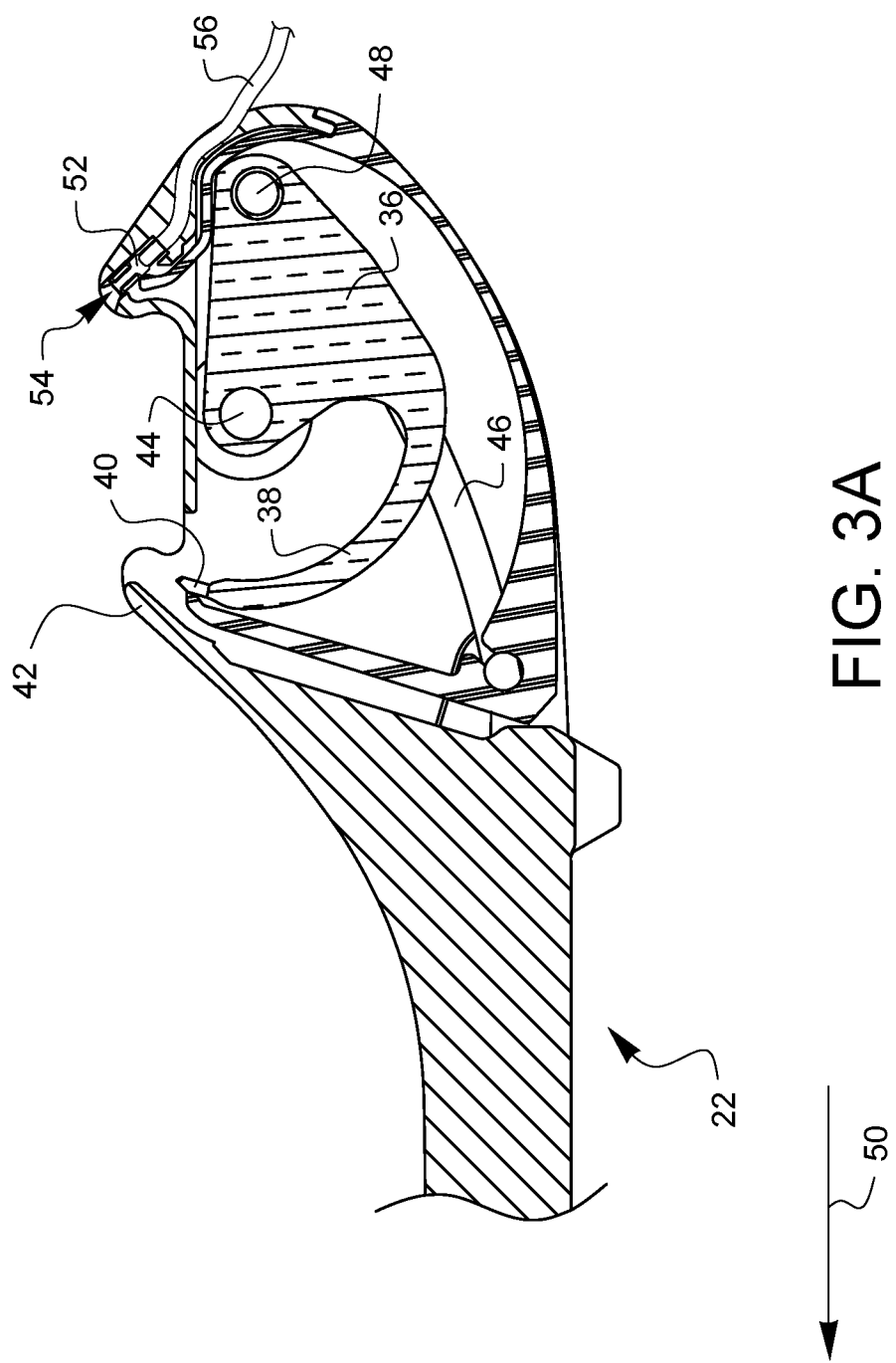
FIG. 3A is a side, partial cross-sectional view of the distal end of the surgical suturing instrument of FIG. 1 illustrating a starting position.
Figure 3B:
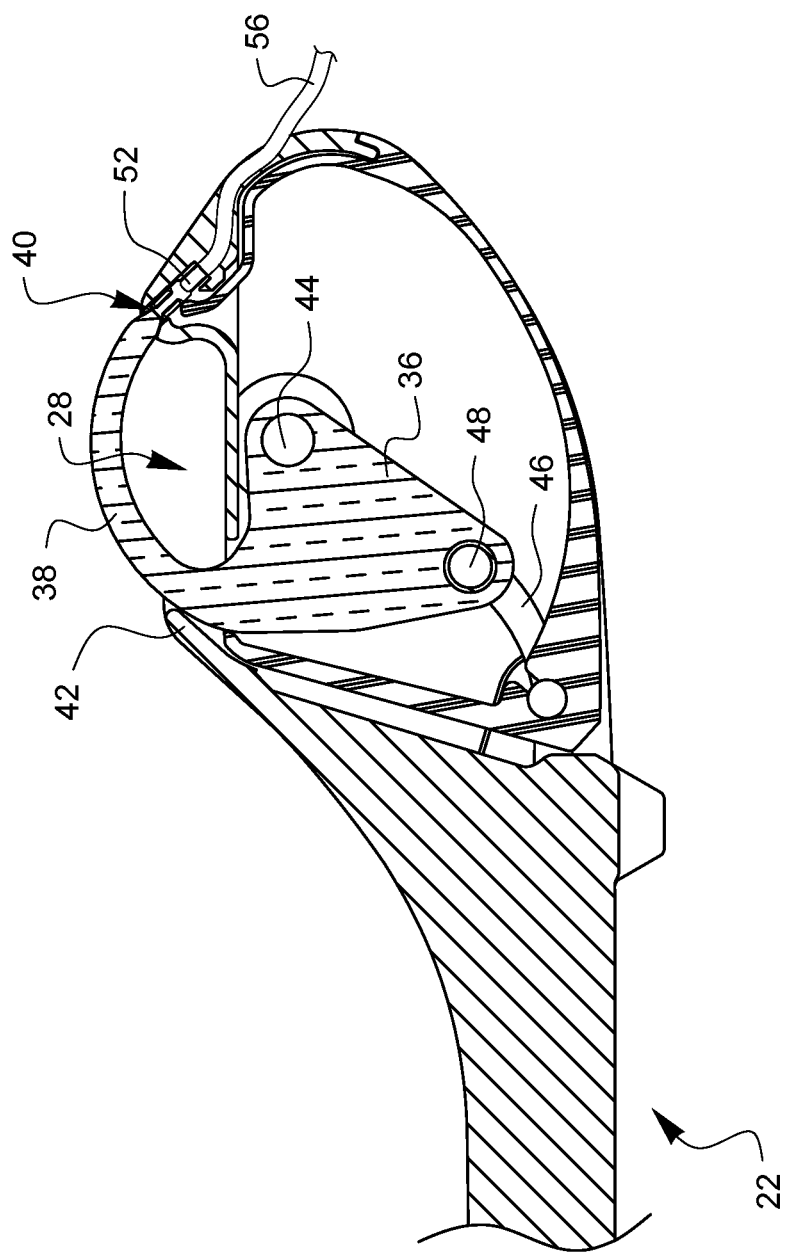
FIG. 3B is a side, partial cross-sectional view of the distal end of the surgical suturing instrument of FIG. 1 illustrating a state after the curved arm and ferrule-engaging tip of a needle have been moved along an arcuate path and into contact with a ferrule.
Figure 3C:
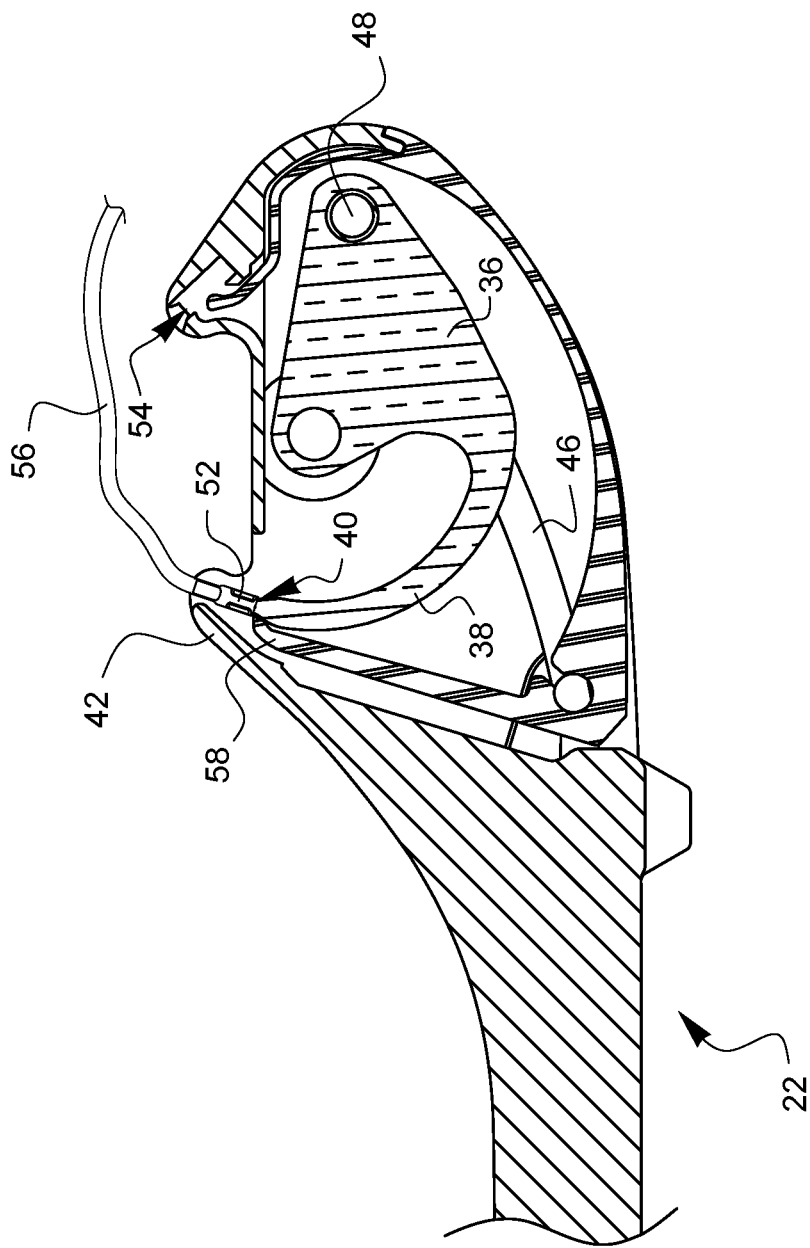
FIG. 3C is a side, partial cross-sectional view of the distal end of the surgical suturing instrument of FIG. 1 illustrating a state where the needle has been rotated back to the starting position.

FIGS. 3A-3C are side, partial cross-sectional views of the distal end 22 of the surgical suturing instrument 20 of FIG. 1. FIG. 3A illustrates a starting position, where the needle 36 has a curved arm 38 with a ferrule-engaging tip 40 which are sitting within a distal tip housing 42. This particular embodiment actually has two curved needle arms and two ferrule-engaging tips, but only one can be seen from this side view. Both needle arms/ferrule engaging tips work similarly, however. The needle 36 may pivot on axle 44 when a control cable 46 coupled to the needle 36 at point 48 is pulled in a proximally 50 by the handle (not visible in this view). A ferrule 52 is seated in a ferrule-receiving aperture 54. The ferrule 52 is attached to one end of a suture 56. The other end of suture 56 is typically attached to another ferrule which is housed in a similar ferrule-receiving aperture for interaction with the other ferrule-engaging tip. The ferrule 52 is sized to couple with the ferrule-engaging tip 40 when the tip 40 is brought into contact with the ferrule 52. FIG. 3B illustrates a state of the distal tip 22 of the instrument 20 after the curved arm 38 and the ferrule-engaging tip 40 have been moved along an arcuate path and into contact with the ferrule 52. If tissue had been present in the tissue bite area 28, then the needle arm 38 would have passed through such tissue. This needle 36 movement may be caused by squeezing the handle 30 shown in FIG. 1. In the position shown in FIG. 3B, the ferrule 52 is coupled to the ferrule-engaging tip 40 of the needle 36. In FIG. 3C, the handle has been released, causing the needle 36 to rotate back to the position of FIG. 3A. Now, however, the suture 56 has been drawn back across the tissue bite area 28, and if tissue had been present, the suture would have been pulled back through the tissue, creating a suture stitch.

A ferrule release feature 58 rides along the needle arm 38 near the ferrule-engaging tip 40. The operator of the surgical instrument may hyper-extend the handle to rotate the needle 36 further in a counter-clockwise direction (as viewed in FIG. 3C) to cause the ferrule release feature 58 to push the ferrule 52 off of the ferrule engaging tip 40. If the surgical suturing instrument is to be used again, however, a new set of ferrules will need to be loaded into the ferrule-receiving apertures (including ferrule-receiving aperture 54 which is visible in this view).

Figure 4A:
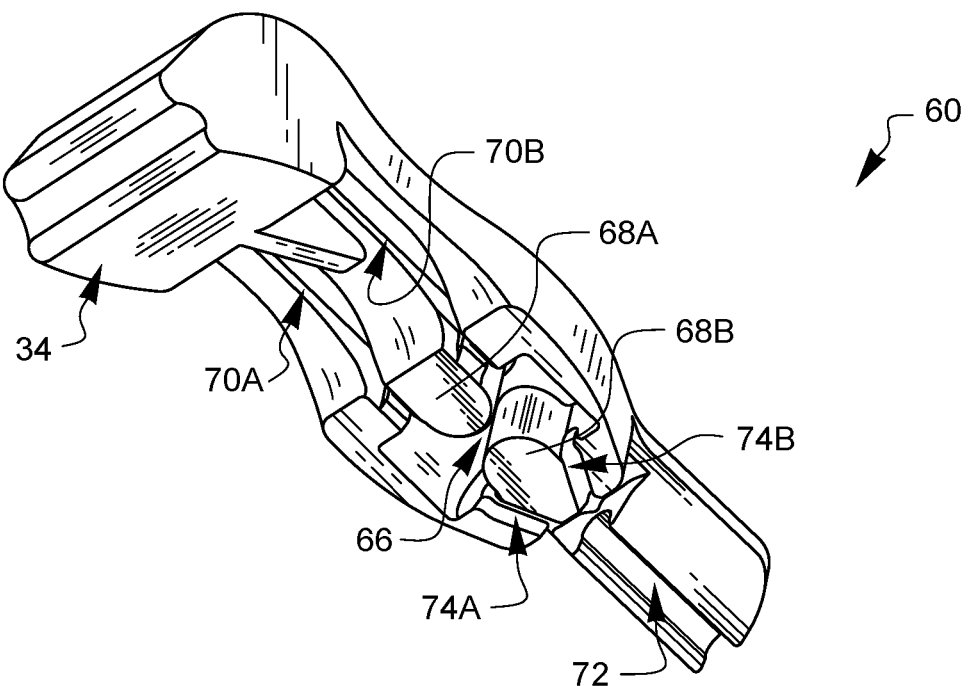
FIGS. 4A and 4B illustrate one embodiment of a quick-load head in a front-bottom-right perspective and front-top-tight perspective, respectively.
Figure 4B:
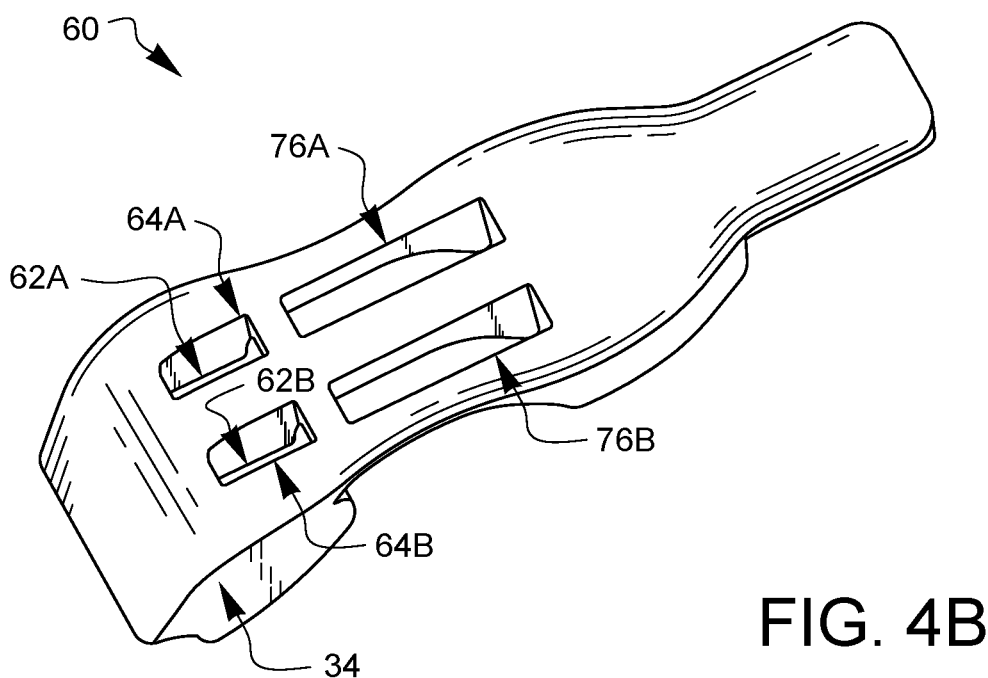

FIGS. 4A and 4B illustrate one embodiment of a quick-load head 60 in a front-bottom-right perspective and front-top-tight perspective, respectively. The quick-load head 60 has a protrusion 34 configured to be releasably held by a tissue bite area of a surgical suturing instrument. In this embodiment, the protrusion 34 defines multiple ferrule-holders 62A, 62B, which may be seen through ferrule-viewing openings 64A, 64B. The quick-load head 60 also has pledget holder 66 formed between protrusions 68A, 68B. Suture channels 70A, 70B lead from respective ferrule-holders 62A, 62B to the area of the pledget holder 66. The quick-load head 60 has a tube interface 72, and another set of suture channels 74A, 74B lead to the tube interface 72. The quick-load head 60 also defines receiving-aperture openings 76A, 76B.

FIGS. 5A, 5B, 5C, 5D, 5E, and 5F are front, left side, right side, rear, top, and bottom elevational views respectively of the quick-load head 60 of FIGS. 4A, 4B.

Figure 6A:
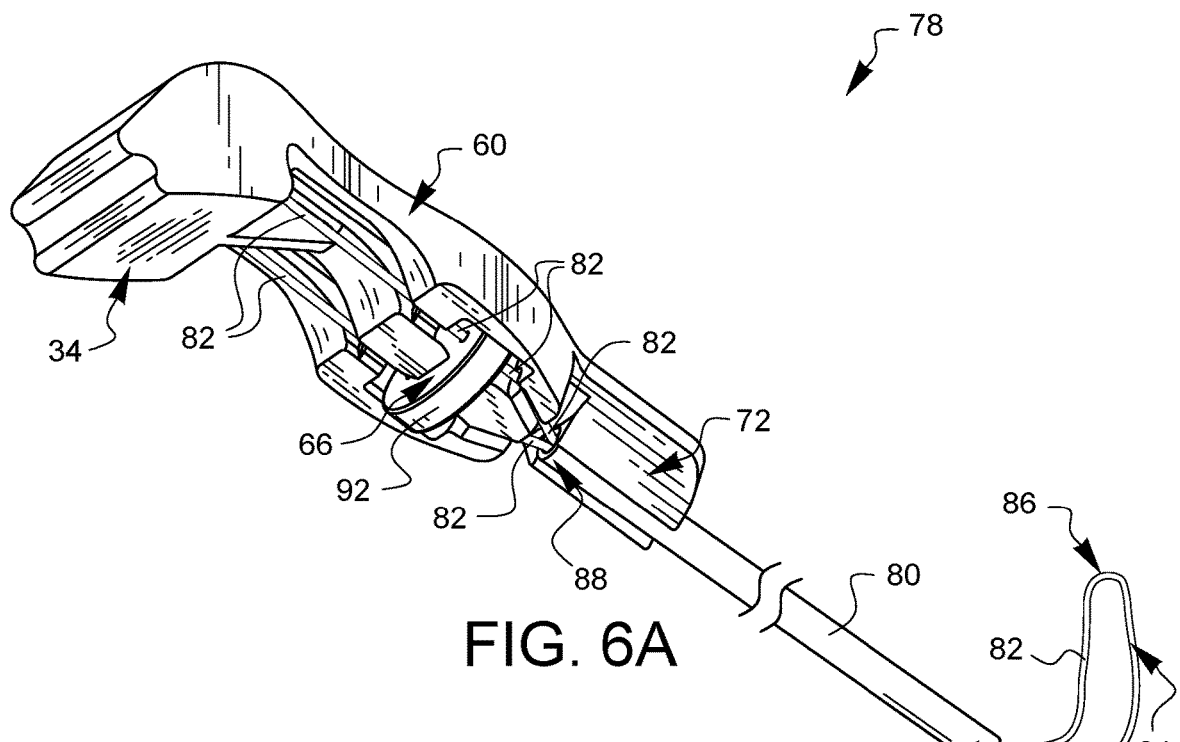
FIGS. 6A and 6B illustrate one embodiment of a loader for surgical suturing from a front-bottom-right perspective and a front-top-right perspective, respectively.
Figure 6B:
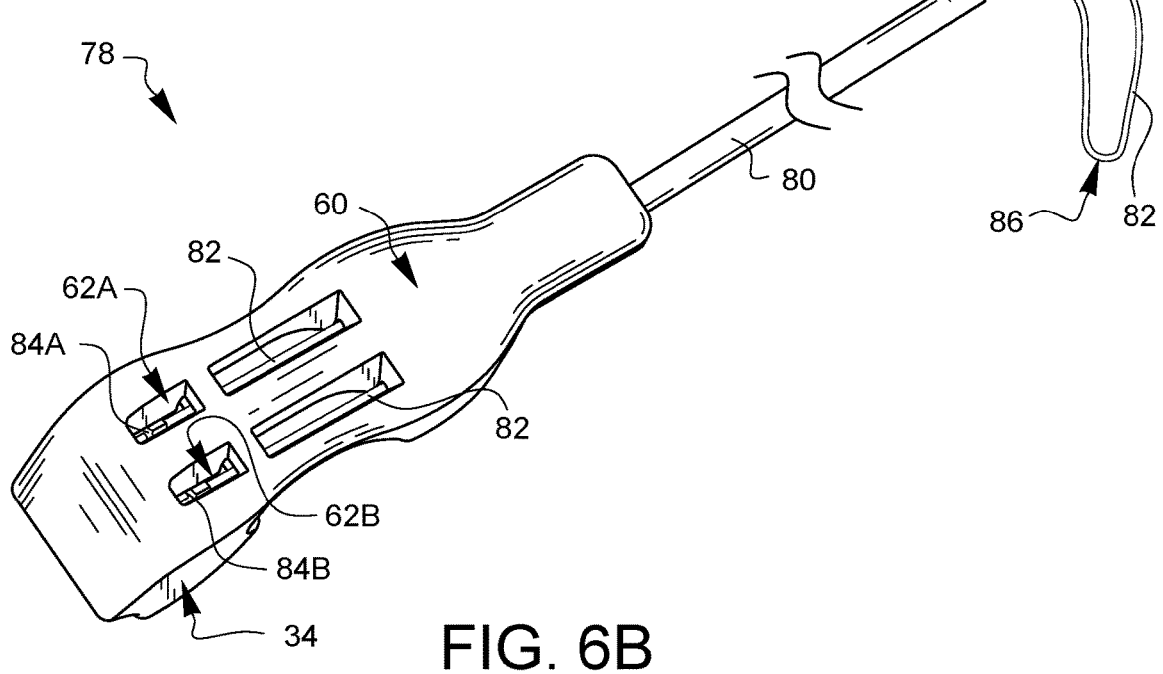

FIGS. 6A and 6B illustrate one embodiment of a loader 78 for surgical suturing from a front-bottom-right perspective and a front-top-right perspective, respectively. The loader 78 has the quick-load head 60 previously discussed, but also includes a tube 80 which is coupled to the tube interface 72. The loader 78 also has a suture 82 with first and second ferrules 84A, 84B attached to its respective ends. In assembly, the suture 82 is folded approximately in half and the approximate mid-point 86 is passed into a first end 88 of the tube 80 and out a second end 90 of the tube 80. The ends of the suture 82 with the ferrules 84A, 84B still protrude from the first end 88 of the tube, and the ferrules 84A, 84B are passed through a pledget 92. The ferrules 84A, 84B are then each placed into their respective ferrule holders 62A, 62B, while the pledget 92 is placed into the pledget holder 66. The tube 80 can be secured to the tube interface 72, and the loop of suture 94 protruding from the second end 90 of the tube 80 may be pulled slightly to take up any suture slack without pulling so hard as to dislodge the ferrules 84A, 84B from the ferrule holders 62A, 62B.

Figure 7A:
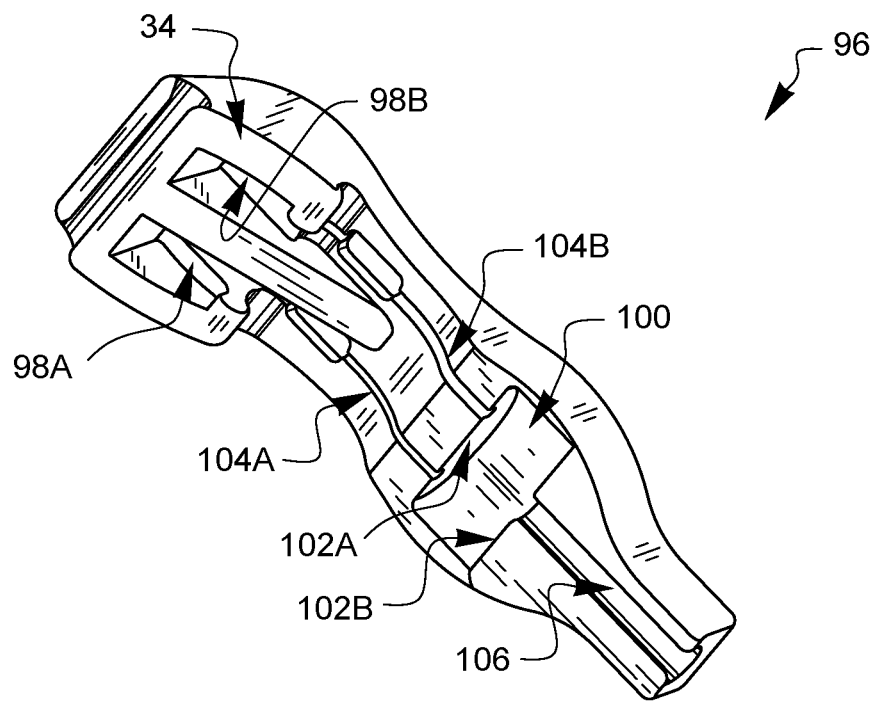
FIGS. 7A and 7B illustrate another embodiment of a quick-load head in a front-bottom-right perspective and front-top-tight perspective, respectively.
Figure 7B:
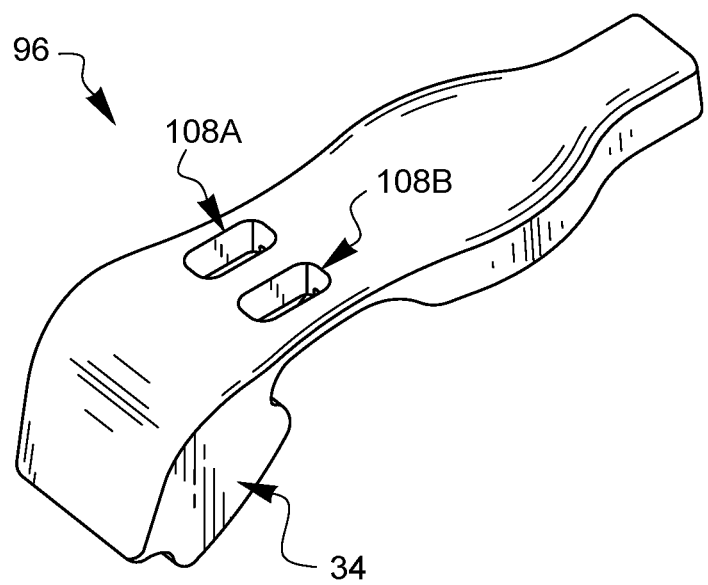
Figure 8E:
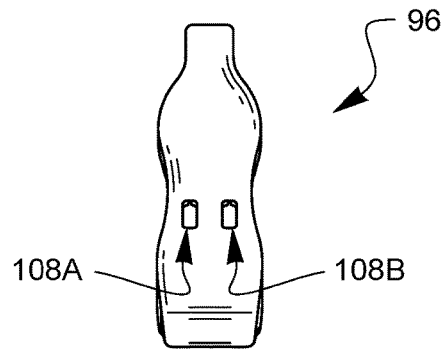
FIGS. 8A, 8B, 8C, 8D, 8E, and 8F are front, left side, right side, rear, top, and bottom elevational views respectively of the quick-load head of FIGS. 7A, 7B.
Figures 8A, 8B, 8C, 8D:
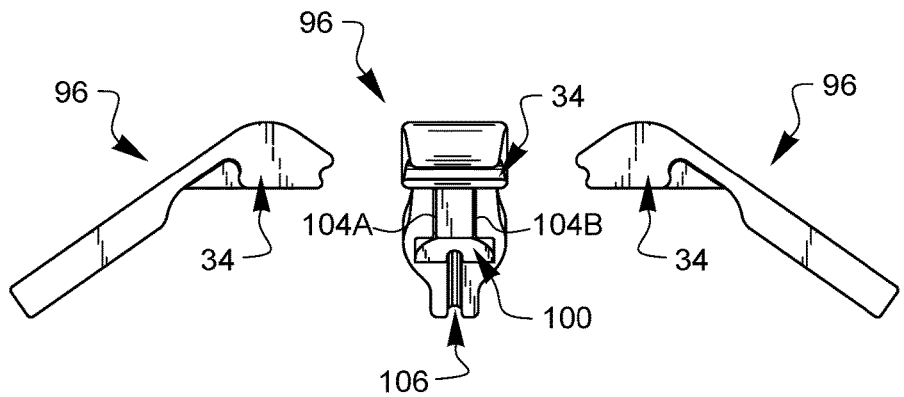
Figure 8F:
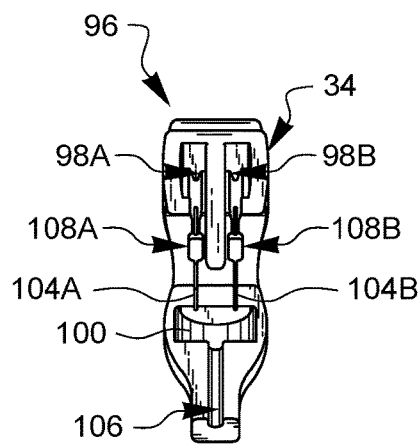

FIGS. 7A and 7B illustrate another embodiment of a quick-load head 96 in a front-bottom-right perspective and front-top-tight perspective, respectively. The quick-load head 96 has a protrusion 34 configured to be releasably held by a tissue bite area of a surgical suturing instrument. In this embodiment, the protrusion 34 defines multiple ferrule-holders 98A, 98B which may be seen from the underside view of FIG. 7A, since this embodiment does not have ferrule-viewing openings on the top to allow ferrules to be seen in the ferrule holders 98A, 9B from the top. The quick-load head 96 also has pledget holder 100 formed between walls 102A, 102B. Suture channels 104A, 104B lead from respective ferrule-holders 98A, 98B to the area of the pledget holder 100. The quick-load head 96 has a tube interface 106 which leads to the pledget holder 100. The quick-load head 96 also defines receiving-aperture openings 108A, 108B.

FIGS. 8A, 8B, 8C, 8D, 8E, and 8F are front, left side, right side, rear, top, and bottom elevational views respectively of the quick-load head 96 of FIGS. 7A, 7B.

Figure 9A:
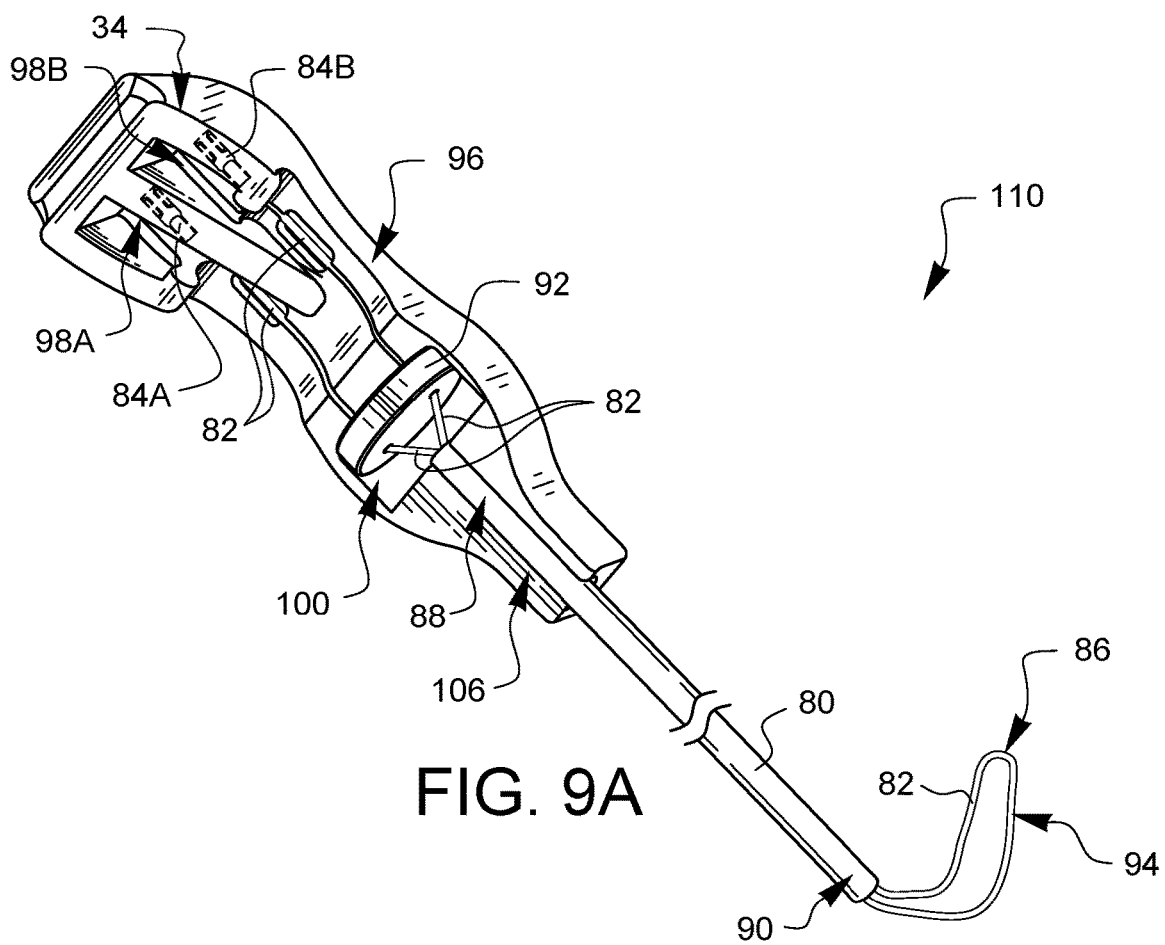
FIGS. 9A and 9B illustrate another embodiment of a loader for surgical suturing from a front-bottom-right perspective and a front-top-right perspective, respectively.
Figure 9B:
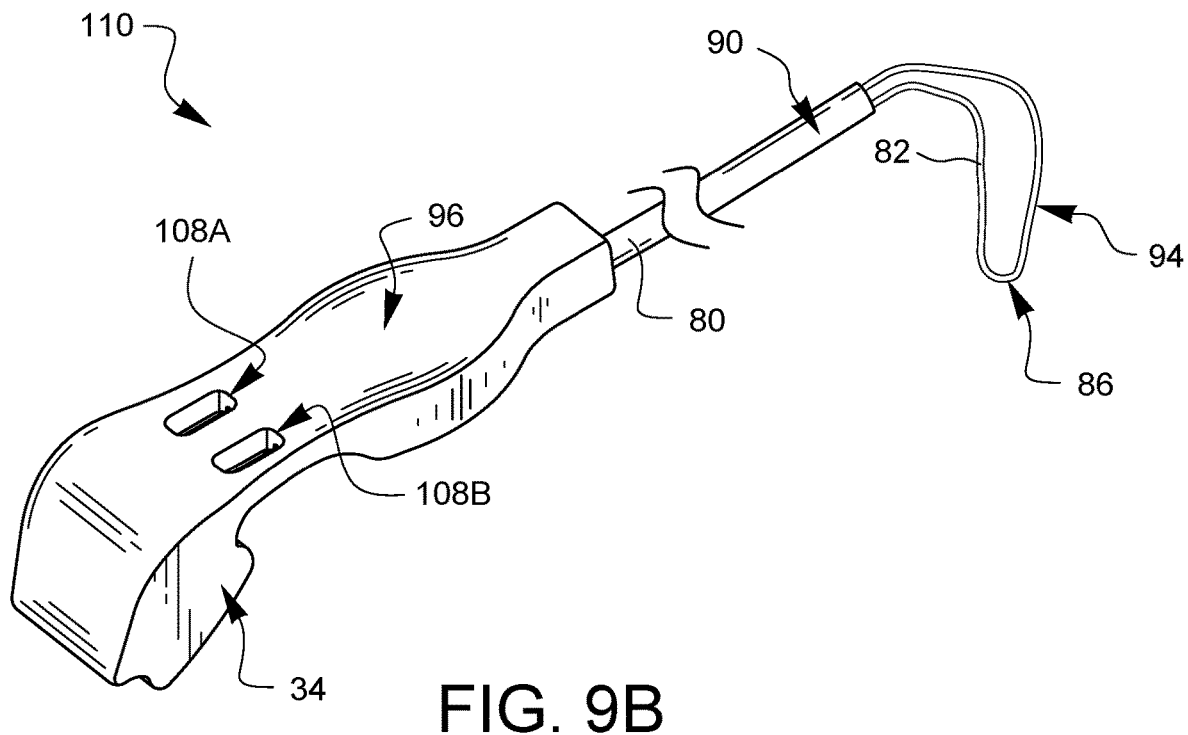

FIGS. 9A and 9B illustrate another embodiment of a loader 110 for surgical suturing from a front-bottom-right perspective and a front-top-right perspective, respectively. The loader 110 has the quick-load head 96 previously discussed, but also includes a tube 80 which is coupled to the tube interface 106. The loader 110 also has a suture 82 with first and second ferrules 84A, 84B attached to its respective ends. In assembly, the suture 82 is folded approximately in half and the approximate mid-point 86 is passed into a first end 88 of the tube 80 and out a second end 90 of the tube 80. The ends of the suture 82 with the ferrules 84A, 84B still protrude from the first end 88 of the tube, and the ferrules 84A, 84B are passed through a pledget 92. The ferrules 84A, 84B are then each placed into their respective ferrule holders 98A, 98B, while the pledget 92 is placed into the pledget holder 100. The tube 80 can be secured to the tube interface 106, and the loop of suture 94 protruding from the second end 90 of the tube 80 may be pulled slightly to take up any suture slack without pulling so hard as to dislodge the ferrules 84A, 84B from the ferrule holders 98A, 98B.

Figure 10A:
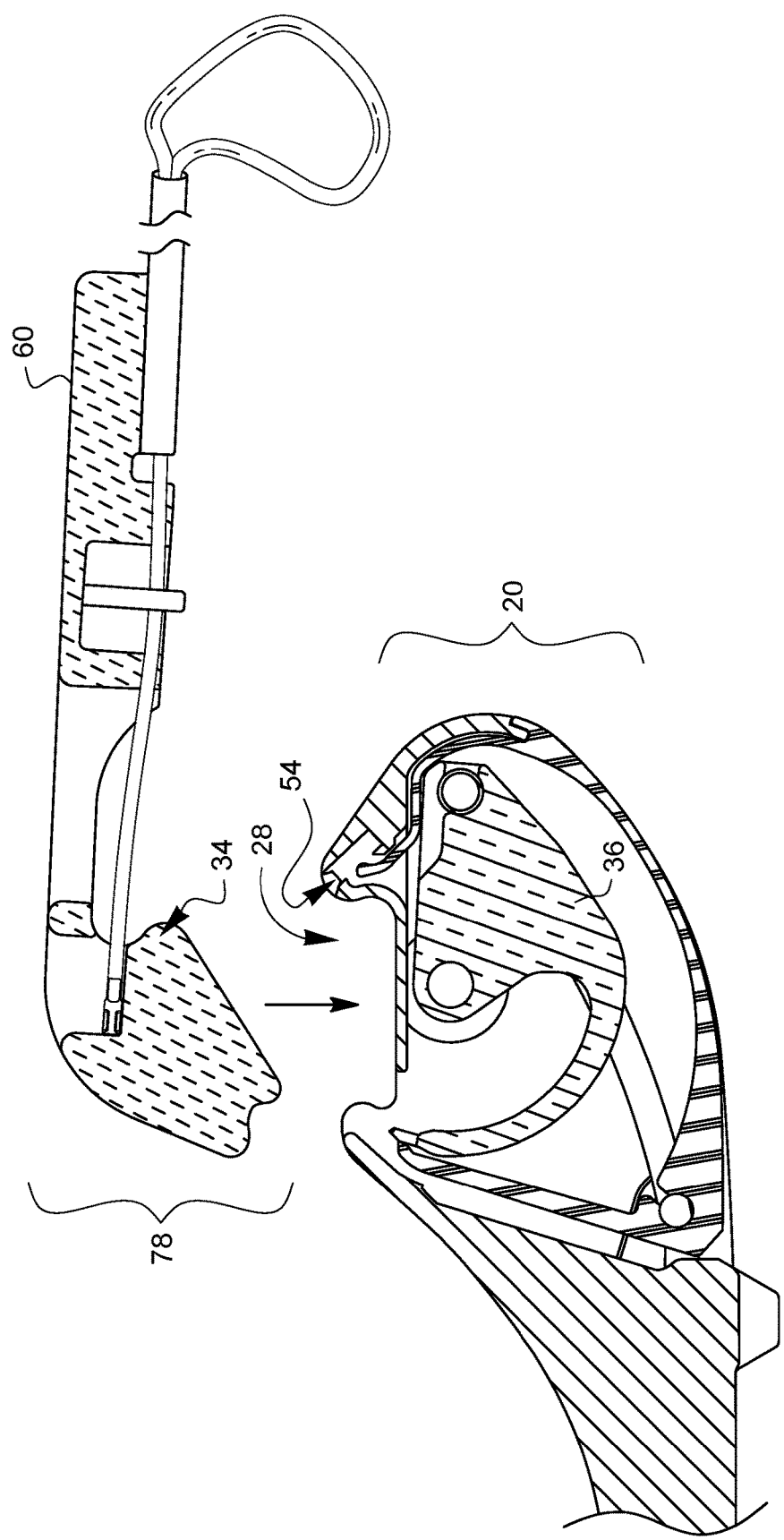
Figure 10B:
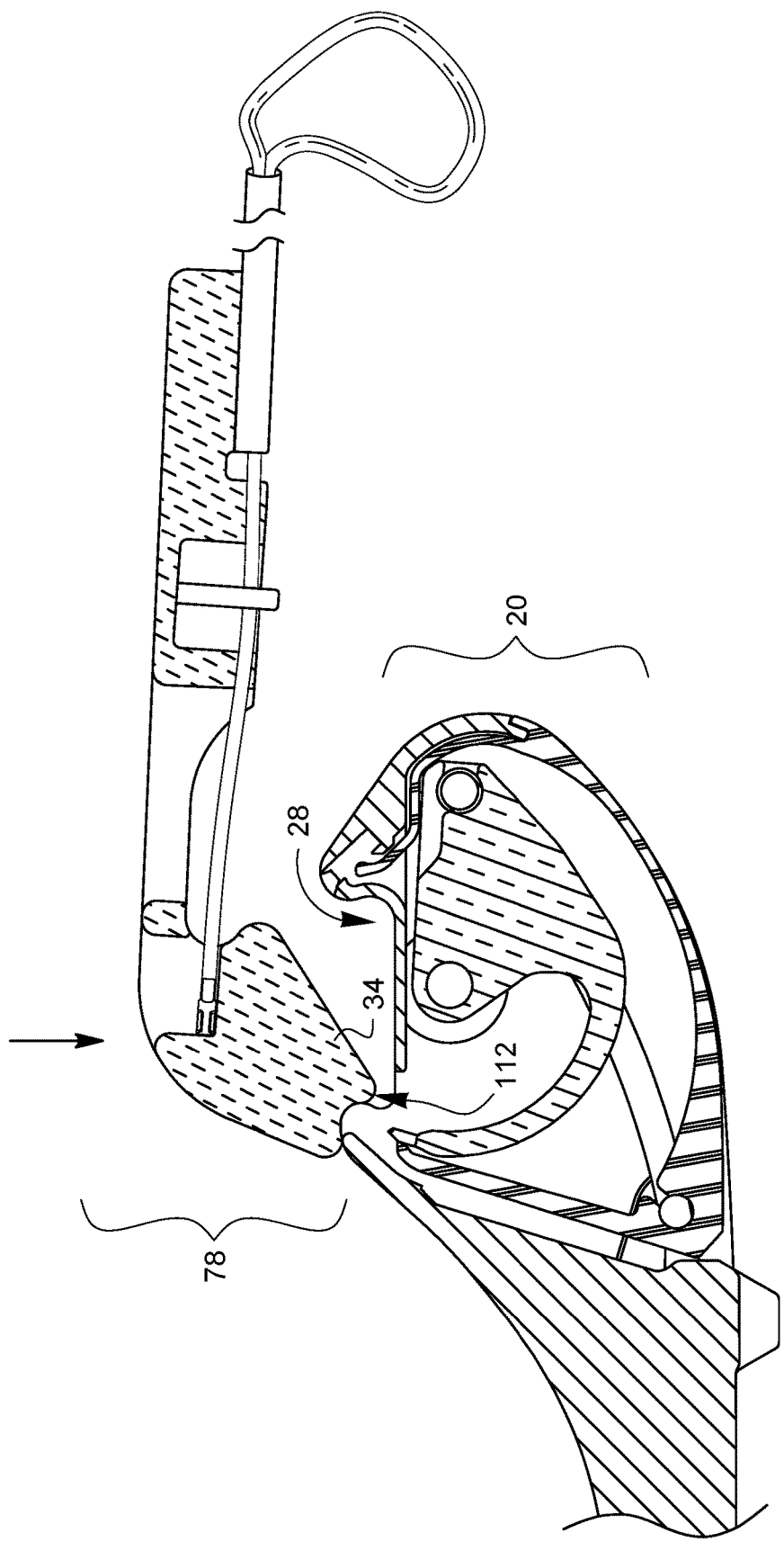
Figure 10C:
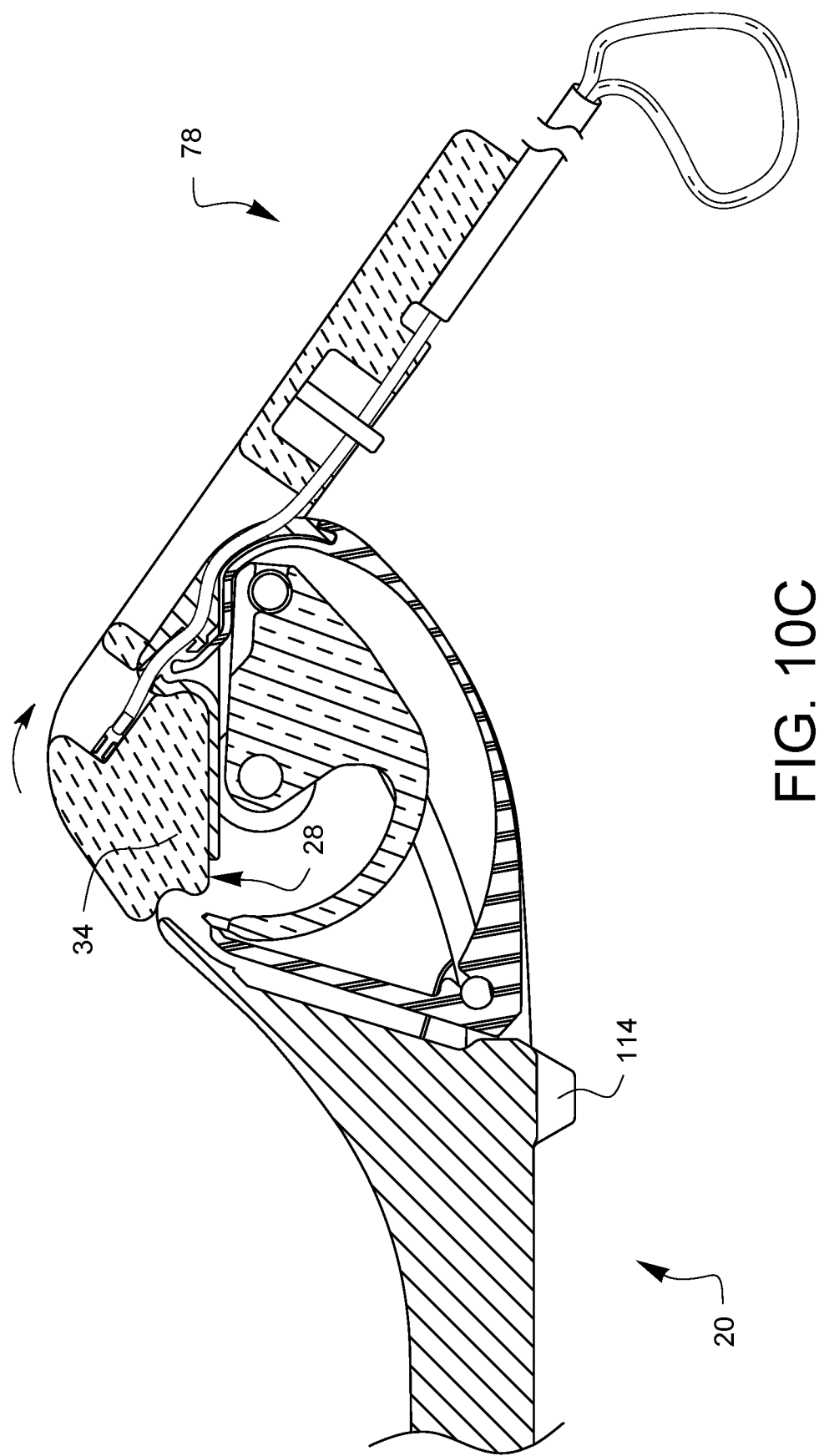
Figure 10D:
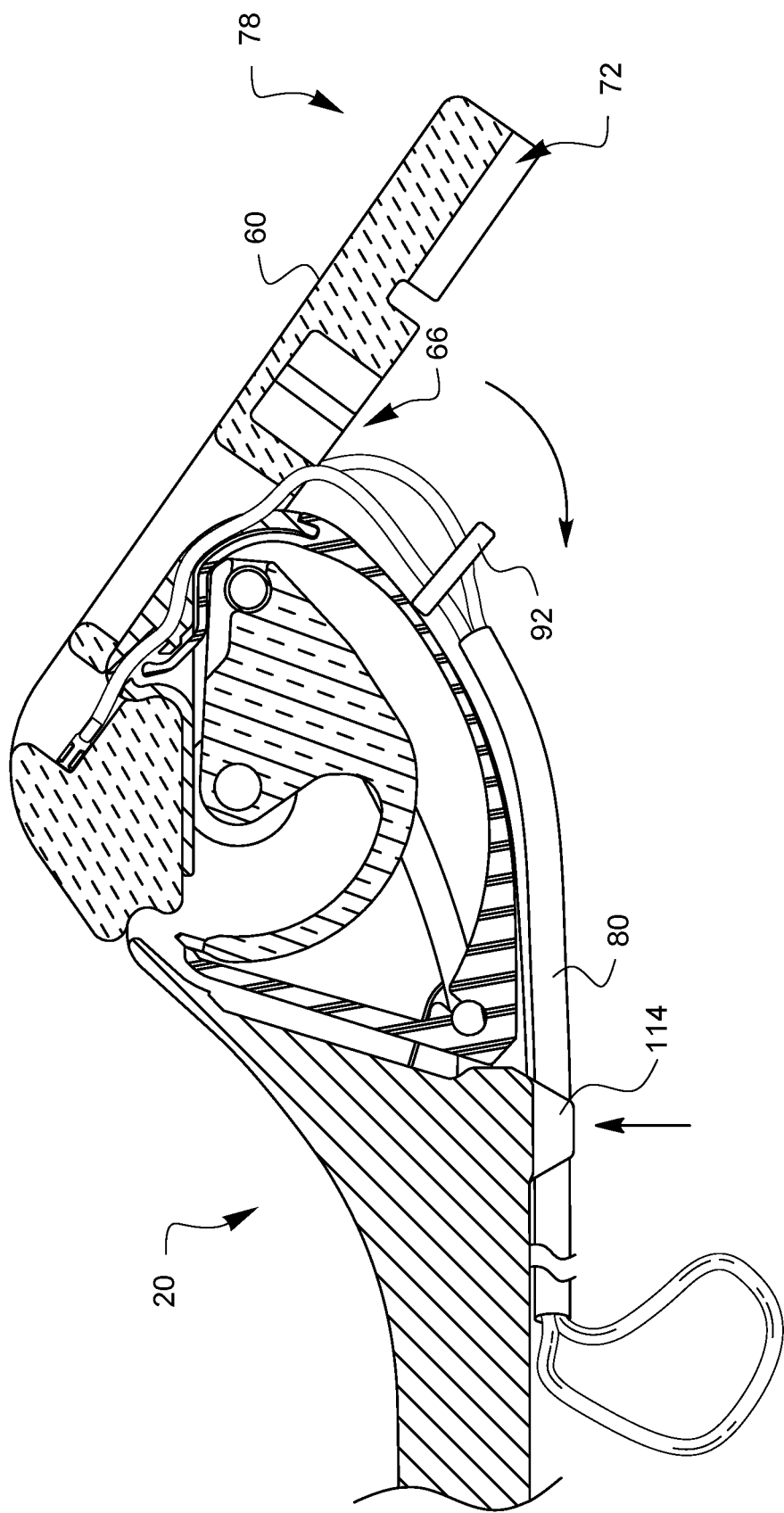

FIGS. 10A to 10G-1 illustrate one embodiment of using a loader, in this case, the loader 78 of FIGS. 6A-6B to load ferrules into a surgical suturing instrument, such as the instrument 20 of FIG. 1. The views of FIGS. 10A to 10G-1 are in partial cross-sectional side view to better illustrate what is going on. Although only one needle tip/ferrule can be seen in these views, it should be understood that the other needle/ferrule is working in a similar fashion. In FIG. 10A, the protrusion 34 of the head 60 of the loader 78 is approaching the tissue bite area 28 of the surgical suturing instrument 20. It should be noted that the ferrule-receiving aperture 54 of the suturing instrument 20 is empty, and the needle 36 is in a retracted position. As shown in FIG. 10B, a leading edge 112 of the loader's protrusion 34 is brought into contact with one side of the tissue bite area 28 on the suturing instrument 20. As shown in FIG. 10C, the loader 78 is then pivoted down until the protrusion 34 fully engages and is held by the tissue bite area 28 of the suturing instrument 20. The suturing device 20 may be equipped with one or more tube holders 114, and as shown in FIG. 10D, the tube 80 may be removed from the tube interface 72 of the loader 78 and bent back towards the suturing instrument 20 so that the tube 80 can be clipped into the one or more tube holders 114. In some embodiments, the act of bending the tube 80 back may dislodge the tube 80 from the tube interface 72. This may also dislodge the pledget 92 from the head 60 of the loader 78. As shown in FIG. 10E, the suturing instrument 20 has a second tube holder 116 molded into an orientation selector 118 on the suturing instrument 20. Some embodiments may have fewer or more tube holders. FIG. 10E-1 is simply an enlarged view of a portion of the distal tip 22 of the surgical suturing instrument 20 of FIG. 10E. The ferrule 84B can be seen held in the ferrule holder 62B, and the suture 82, which is aligned with a slot in the end of the suturing instrument 20 leading to the ferrule-receiving aperture 54, has been moved into the ferrule receiving aperture 54. As shown in FIG. 10F, the loop 94 of suture 82 can be pulled 118 away from the end 90 of the tube 80, causing the ferrule 84B to be pulled into the ferrule-receiving aperture 54. FIG. 10F-1 is an enlarged view which better shows the ferrule 84B seated in the ferrule-receiving aperture. The user can see the ferrule 84B has been properly seated through the receiving-aperture opening 76B and can stop pulling the suture loop 94. The second ferrule (not visible in this view) is similarly seated by the pulling of the suture loop 94, which pulls both ferrules 84A, 84B at substantially the same time once any slack is out of the suture 82. As shown in FIG. 10G and the enlarged view of FIG. 10G-1, the quick-load head 60 can be removed 120 from the tissue bite area 28 of the suturing instrument 20. The tube 80 may be left in place to help keep the suture 82 organized prior to stitch placement. The ferrules are placed in the instrument 20 and ready for use in suturing. The suture 82 can be pulled out of the tube 80 whenever desired.

The quick loader has the advantage that it is much easier to align with the device suturing instrument than it would be to manually align the tiny ferrules with the ferrule-receiving apertures. Furthermore, multiple ferrules may be loaded at the same time with a single motion. This allows for surgeons to save time, which can reduce fatigue and potentially reduce the amount of time a patient is coupled to a cardio-pulmonary bypass machine (for cardiac procedures). This can help improve patient outcomes and save hospitals money.

Figure 11:
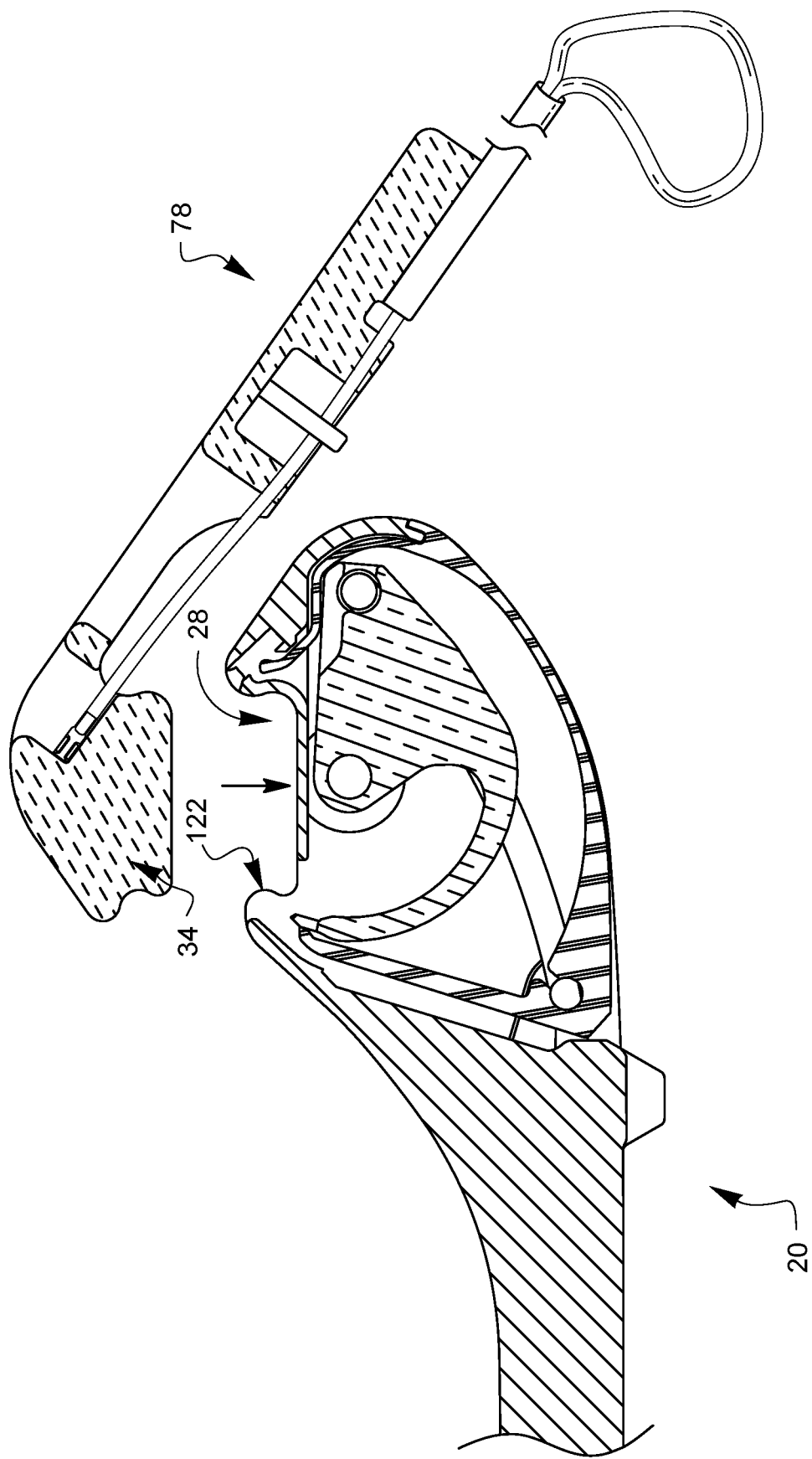
FIG. 11 illustrates an alternate method of attaching the loader of FIGS. 6A-6B to a surgical suturing instrument.

In the example of FIGS. 10A to 10G1, the loader 78 is inserted into the tissue bite area 28 using a pivoting motion. As illustrated in FIG. 11, other embodiments may be configured so that the protrusion 34 of the loader 78 may be held by the tissue bite area 28 of the suturing instrument 20 by pressing the protrusion 34 straight down into the tissue bite area. To do this, the protrusion 34 may need to be made of a deformable and/or elastic material that can compress to get past any edges 122 of the tissue bite area 28 which could be in the way.

Figure 12A:
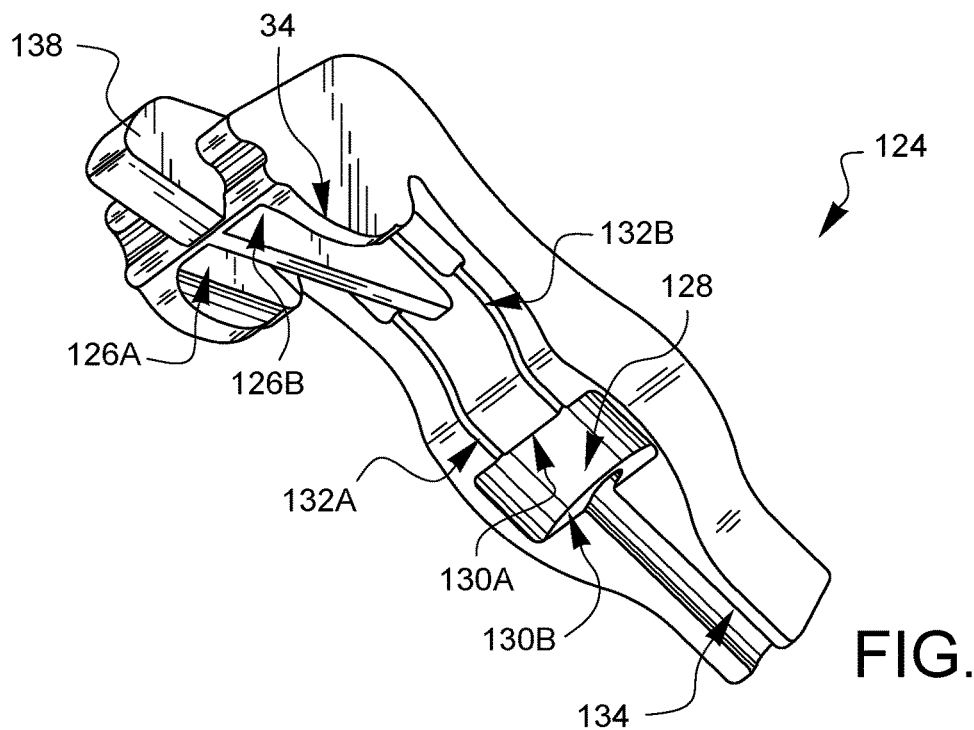
FIGS. 12A and 12B illustrate another embodiment of a quick-load head in a front-bottom-right perspective and front-top-tight perspective, respectively.
Figure 12B:
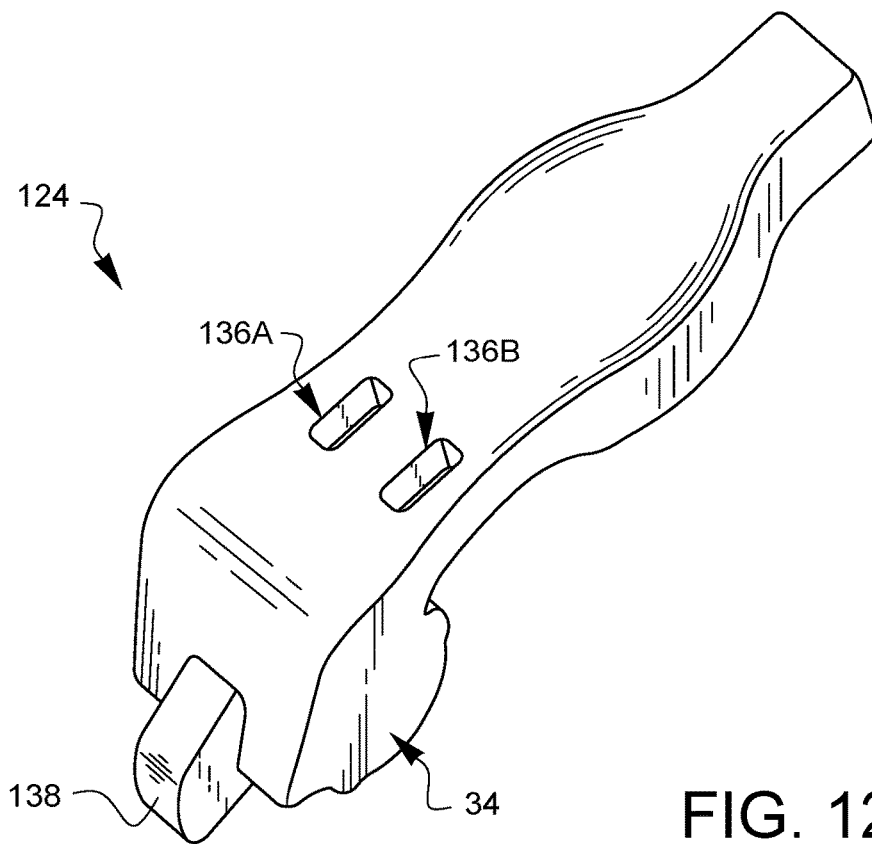

FIGS. 12A and 12B illustrate another embodiment of a quick-load head 124 in a front-bottom-right perspective and front-top-tight perspective, respectively. The quick-load head 124 has a protrusion 34 configured to be releasably held by a tissue bite area of a surgical suturing instrument. In this embodiment, the protrusion 34 defines multiple ferrule-holders 126A, 126B which may be seen from the underside view of FIG. 12A, since this embodiment does not have ferrule-viewing openings on the top to allow ferrules to be seen in the ferrule holders 126A, 126B from the top. The quick-load head 124 also has pledget holder 128 formed between walls 130A, 130B. Suture channels 132A, 132B stand between respective ferrule-holders 126A, 126B and the area of the pledget holder 128. The quick-load head 124 has a tube interface 134 which leads to the pledget holder 128. The quick-load head 124 also defines receiving-aperture openings 136A, 136B. This embodiment also has an alignment guide 138 configured to align the protrusion 34 with the tissue bite area when installing the quick loader into the tissue bite area.

FIGS. 13A, 13B, 13C, 13D, 13E, and 13F are front, left side, right side, rear, top, and bottom elevational views respectively of the quick-load head 124 of FIGS. 12A, 12B.

Figure 14A:
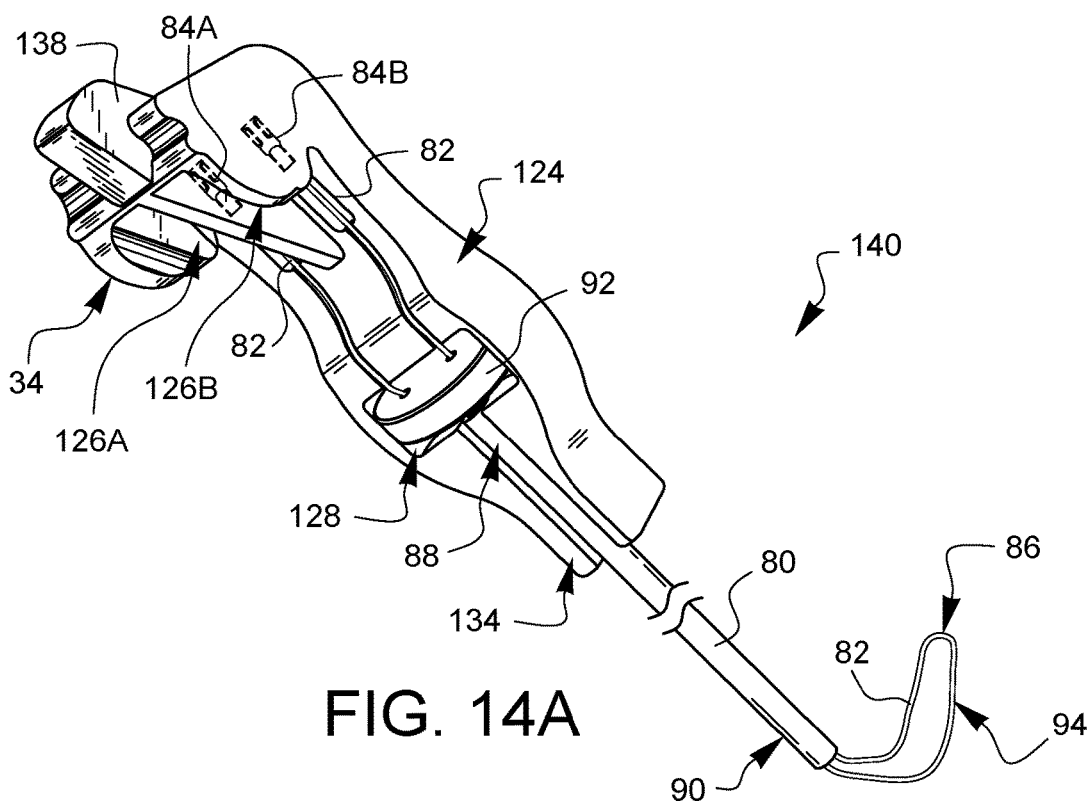
FIGS. 14A and 14B illustrate another embodiment of a loader for surgical suturing from a front-bottom-right perspective and a front-top-right perspective, respectively.
Figure 14B:
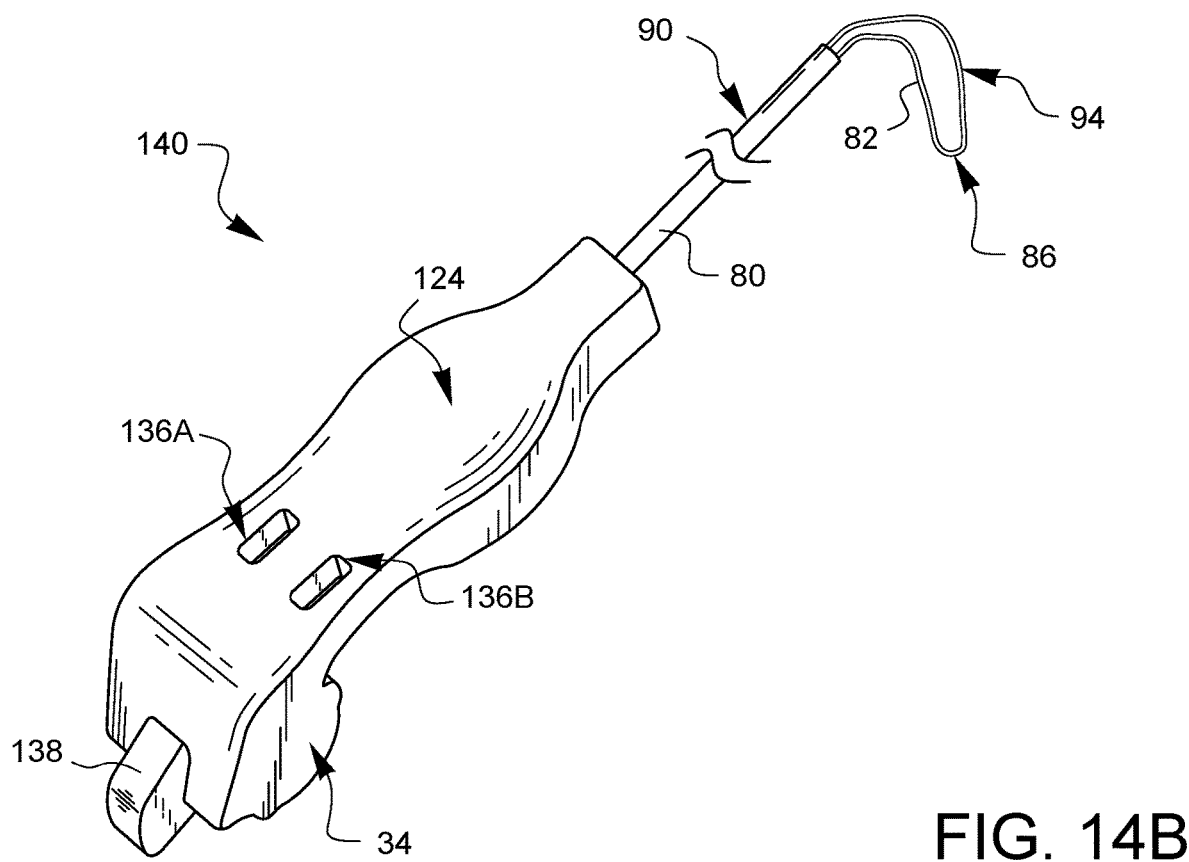

FIGS. 14A and 14B illustrate another embodiment of a loader 140 for surgical suturing from a front-bottom-right perspective and a front-top-right perspective, respectively. The loader 140 has the quick-load head 124 previously discussed, but also includes a tube 80 which is coupled to the tube interface 134. The loader 140 also has a suture 82 with first and second ferrules 84A, 84B attached to its respective ends. In assembly, the suture 82 is folded approximately in half and the approximate mid-point 86 is passed into a first end 88 of the tube 80 and out a second end 90 of the tube 80. The ends of the suture 82 with the ferrules 84A, 84B still protrude from the first end 88 of the tube, and the ferrules 84A, 84B are passed through a pledget 92. The ferrules 84A, 84B are then each placed into their respective ferrule holders 126A, 126B, while the pledget 92 is placed into the pledget holder 128. The tube 80 can be secured to the tube interface 134, and the loop of suture 94 protruding from the second end 90 of the tube 80 may be pulled slightly to take up any suture slack without pulling so hard as to dislodge the ferrules 84A, 84B from the ferrule holders 126A, 126B.

Figure 15A:
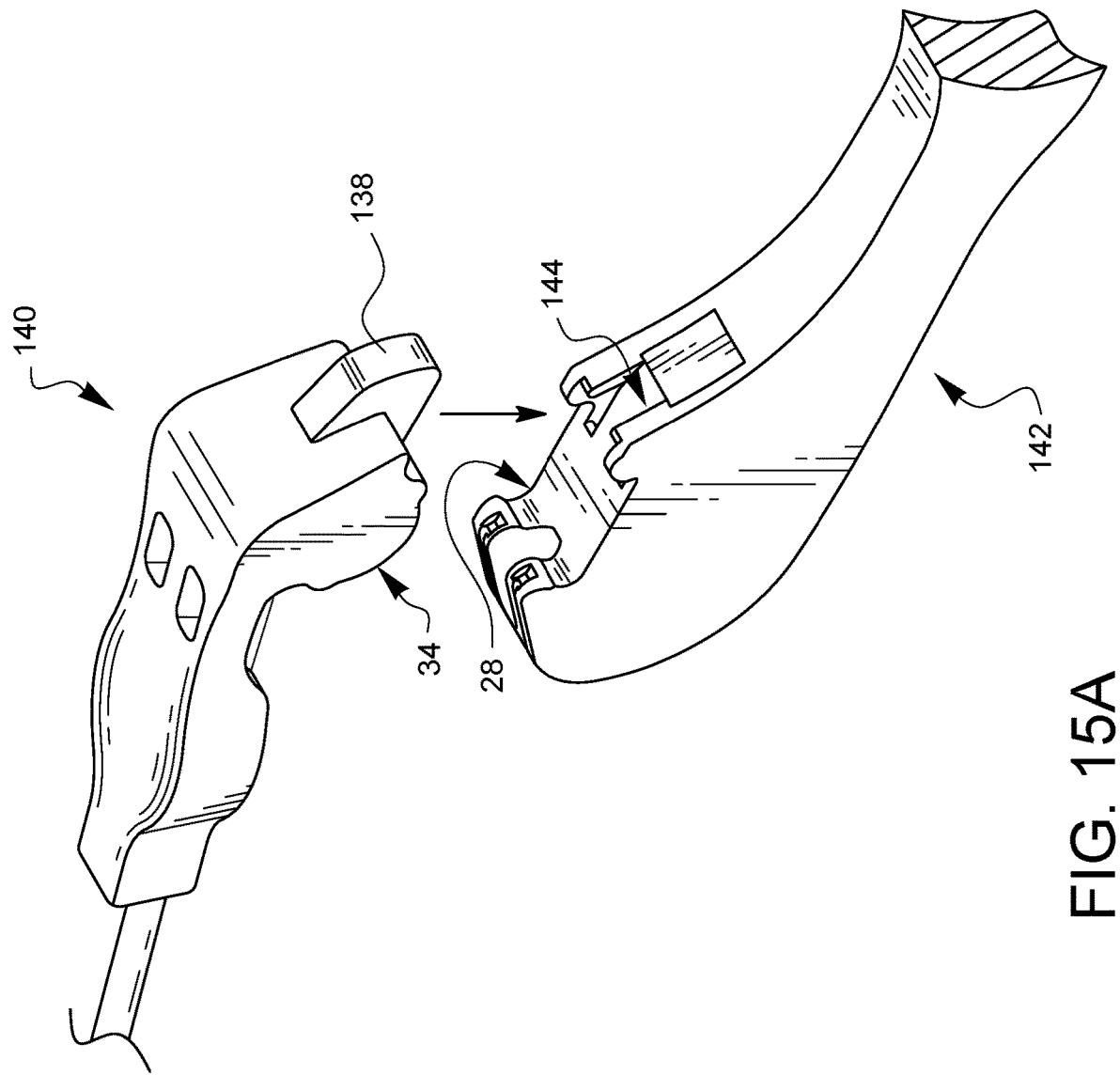
FIGS. 15A-15C schematically illustrate how the loader of FIGS. 14A-14B having an alignment guide and a protrusion configured to be releasably held by a tissue bite area of a surgical suturing instrument might interact.
Figure 15B:
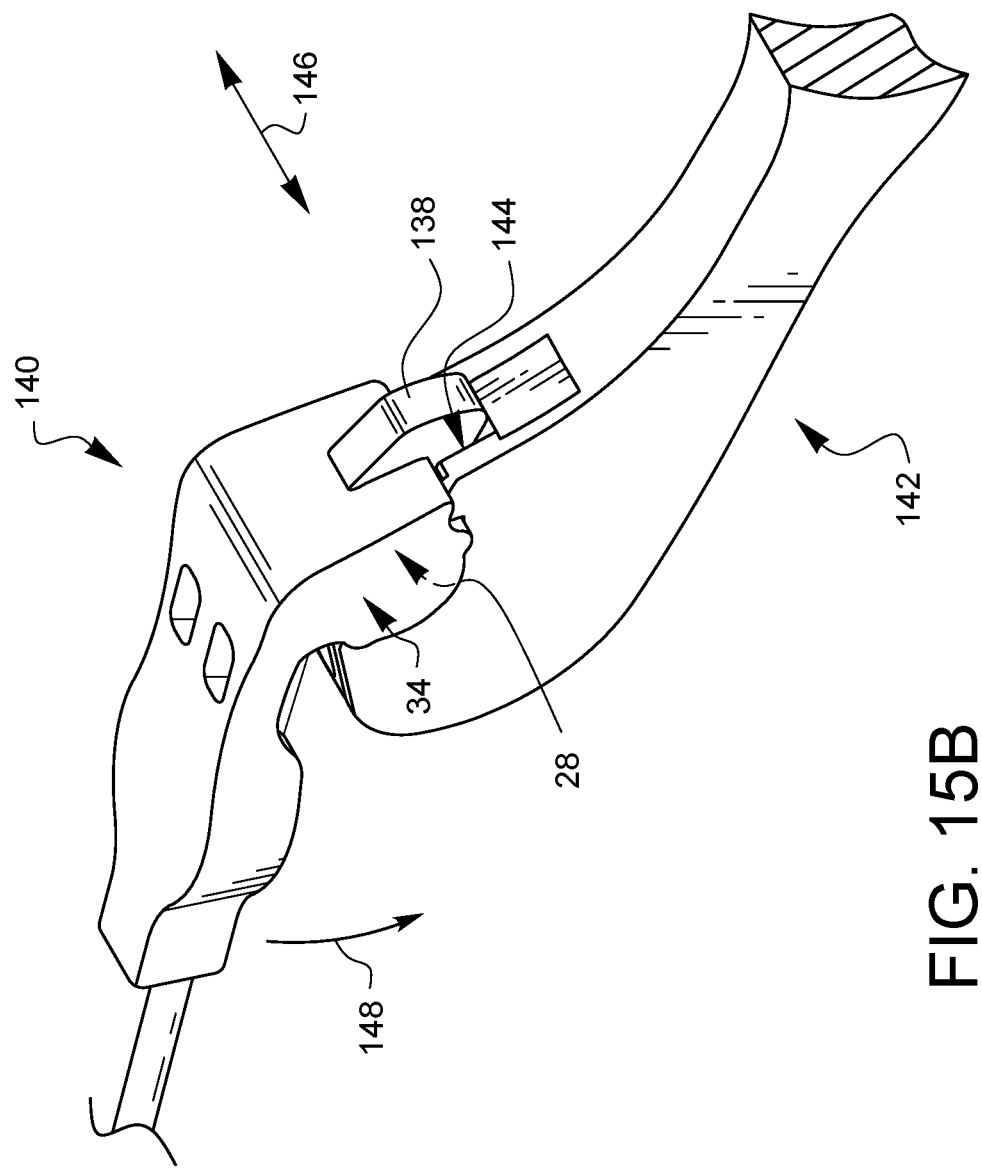
Figure 15C:
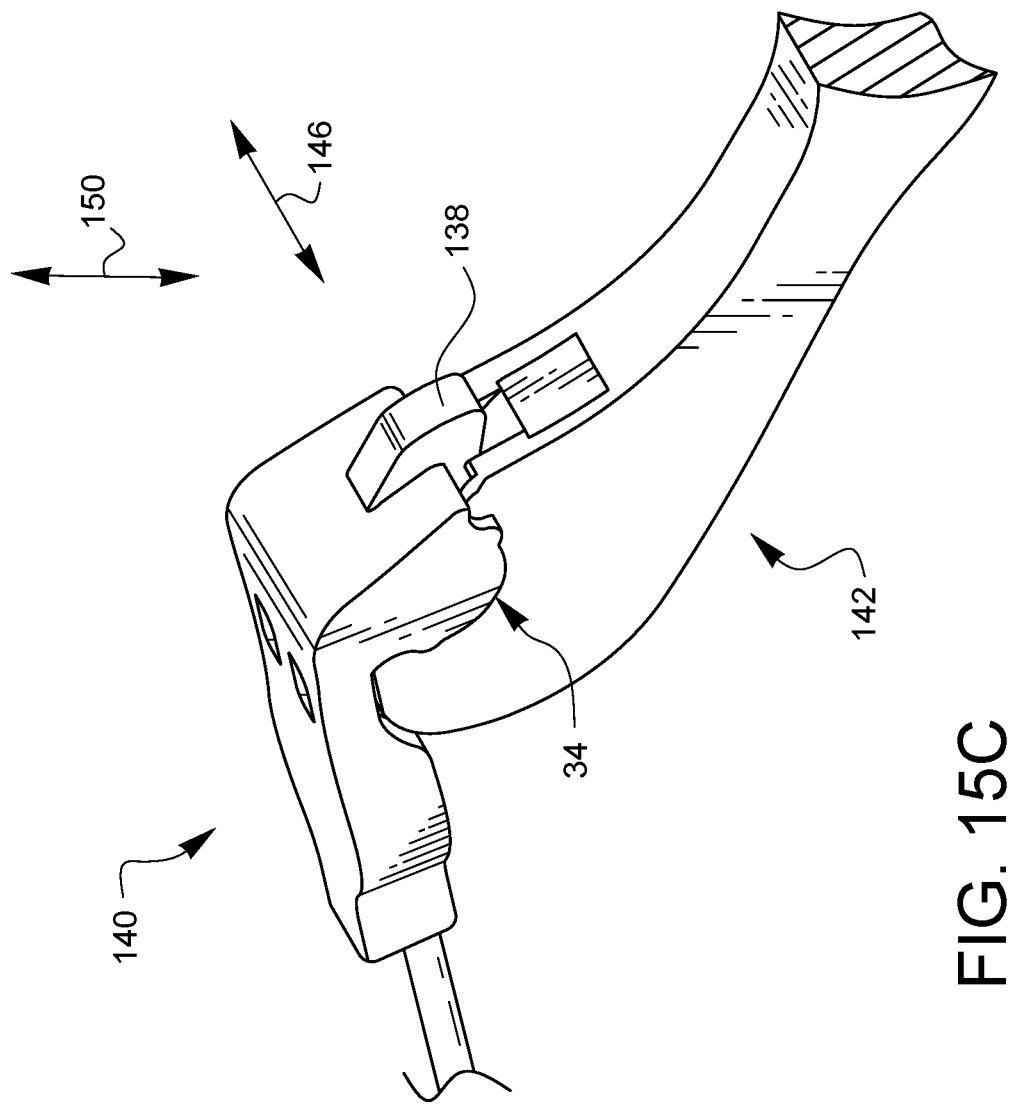
Figure 16E:
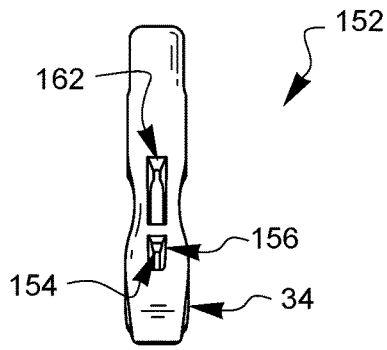
FIGS. 16A, 16B, 16C, 16D, 16E, and 16F illustrate front, left, right, back, top, and bottom views, respectively, of a further embodiment of a quick load head.
Figures 16A, 16B, 16C, 16D:
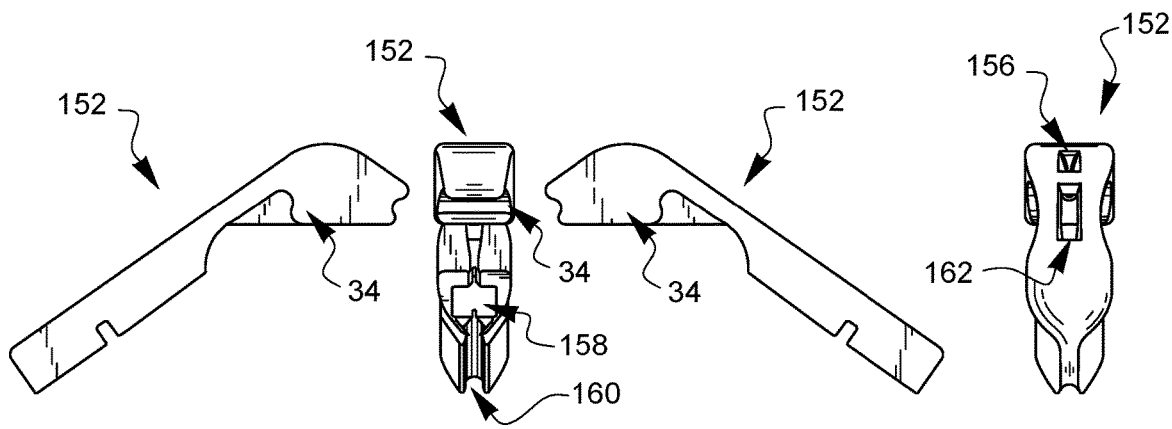
Figure 16F:
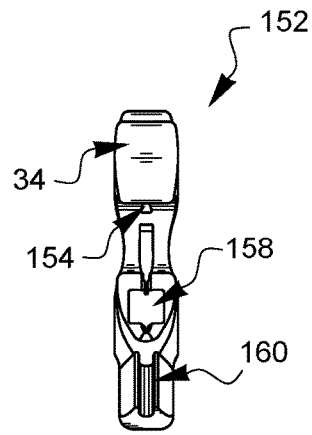

FIGS. 15A-15C schematically illustrate how the loader 140 having an alignment guide 138 and a protrusion 34 configured to be releasably held by a tissue bite area 28 of a surgical suturing instrument 142 might interact. As shown in FIG. 15A, the alignment guide 138 is brought down into a corresponding feature 144 on the surgical suturing instrument 142. As shown in FIG. 15B, the alignment guide 138 engages the corresponding feature 144 so that the loader 140 is constrained in a first direction 146. Next, the loader 144 is pivoted 148 to bring the protrusion 34 around and into contact with the tissue bite area 28 so that the tissue bite area can releasably hold the protrusion 34 as shown in FIG. 15C. Now, the loader 140 is constrained in both a first direction 146 and a second direction 150. At the same time, the loader 140 is more carefully aligned with the instrument 142, making it more likely that the ferrules in the loader 140 will be properly aligned with the ferrule-receiving apertures of the instrument 142.

The preceding examples of loaders all included holders for two ferrules. FIGS. 16A, 16B, 16C, 16D, 16E, and 16F illustrate front, left, right, back, top, and bottom views, respectively, of a quick-load head 152 similar to the quick-load head 60 of FIGS. 4A-4B, but with only a single ferrule holder 154. The quick-load head 152 has a protrusion 34 configured to be releasably held by a tissue bite area of a surgical suturing instrument. In this embodiment, the protrusion 34 defines a ferrule-holder 154, which may be seen through ferrule-viewing opening 156. The quick-load head 152 also has pledget holder 158. The quick-load head 152 has a tube interface 160. The quick-load head 152 also defines a receiving-aperture opening 162.

Various advantages of a loader for a surgical suturing instrument have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. As some non-limiting examples, other embodiments may not have a pledget or a pledget holder; other embodiments may not include a tube or a tube interface; and other embodiments may not include one or more receiving-aperture openings. These alterations, improvements, and modifications are intended to be suggested hereby, and are within the spirit and the scope of the claimed invention. It will be appreciated that for purposes of clarity and where deemed appropriate, reference numerals have been repeated in the figures to indicate corresponding features, and that the various elements in the drawings have not necessarily been drawn to scale in order to better show the features. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A loader adapted to be coupled to a surgical suturing instrument, the loader comprising:
    a head extending along a head axis from a first end to a second end;
    a first protrusion extending along a first protrusion axis from a first end to a second end, wherein the first protrusion axis is parallel to or aligned with the head axis, wherein the first end of the first protrusion is at or adjacent to the first end of the head, and wherein the first protrusion is configured to be brought into contact pivotably with and releasably held by one or more surfaces of the surgical suturing instrument that define a first portion of a tissue bite area of the surgical suturing instrument;
    a tube interface defined by at least one surface that extends along a first portion of the head, the tube interface configured to releasably hold a tube that encloses a first portion of suture; and
    one or more ferrule holders that are each configured to hold a ferrule that is coupled to an end portion of the suture, the one or more ferrule holders being defined by at least one surface that extends along a second portion of the head, the at least one surface extending along a ferrule holder axis that is parallel to the head axis, each of the one or more ferrule holders extending from a first end to a second end along the ferrule holder axis, the first end of the at least one ferrule holder being offset from the first end of the head such that the first end of the at least one ferrule holder is disposed between the first end and the second end of the protrusion.

2. The loader of claim 1, further comprising a pledget holder.

3. The loader of claim 1, further comprising one or more ferrule-viewing openings, wherein each of the one or more ferrule-viewing openings are apertures disposed in the head that are configured to allow a user to view the ferrule held in each corresponding ferrule holder.

4. The loader of claim 1, further comprising an alignment guide configured to mate with the tissue bite area to achieve proper alignment between the ferrule held by each of the one or more ferrule holders and one or more corresponding needles of the surgical suturing instrument.

5. The loader of claim 1, further comprising a second protrusion extending along a second protrusion axis from a first end to a second end, wherein the first protrusion axis is parallel to the head axis and transversely offset from the head axis in a first direction, and the second protrusion axis is parallel to the head axis and transversely offset from the head axis in a second direction, the second protrusion configured to be brought into contact pivotably with and releasably held by one or more surfaces of the surgical instrument that define a second portion of the tissue bite area of the surgical instrument.

6. The loader of claim 5, wherein each of the first protrusion and the second protrusion are planar.

7. The loader of claim 1, wherein the tube interface extends along a tube interface axis from a first end to a second end, wherein the tube interface axis is parallel to or aligned with the head axis.

8. The loader of claim 7, further comprising one or more suture channels leading to the tube interface, wherein each of the one or more suture channels is a groove formed by one or more surfaces of the head, and wherein each of the one or more suture channels is configured to retain a second portion of suture.

9. The loader of claim 7, wherein the second end of the tube interface axis is at or adjacent to the second end of the head.

10. The loader of claim 1, wherein the head is defined in part by a first lateral surface and a second lateral surface, the first lateral surface extending along a first lateral surface axis that is parallel to the head axis and transversely offset from the head axis in a first direction, and the second lateral surface extending along a second lateral surface axis that is parallel to the head axis and transversely offset from the head axis in a second direction, and wherein the first protrusion extends transversely between the first lateral surface and the second lateral surface.

11. The loader of claim 10, wherein each of the first lateral surface and the second lateral surface are non-planar.

12. The loader of claim 1, wherein the at least one surface defining each of the one or more ferrule holders defines a cavity that is configured to retain the ferrule.

13. The loader of claim 1, further comprising the ferrule coupled to the end portion of the suture that is held in each of the one or more ferrule holders.

14. The loader of claim 1, wherein the second end of the at least one ferrule holder is offset from the second end of the head such that the second end of the at least one ferrule holder is disposed at or adjacent to the second end of the protrusion.

* * * * *